US 9,880,111 B2

United States Patent
Oda

(10) Patent No.: US 9,880,111 B2
(45) Date of Patent: Jan. 30, 2018

(54) RADIOGRAPHIC IMAGING SYSTEM AND SYSTEM OPERATION METHOD

(71) Applicant: FUJIFILM Corporation, Tokyo (JP)

(72) Inventor: Yasufumi Oda, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 632 days.

(21) Appl. No.: 14/479,922

(22) Filed: Sep. 8, 2014

(65) Prior Publication Data

US 2015/0071414 A1    Mar. 12, 2015

(30) Foreign Application Priority Data

Sep. 9, 2013  (JP) .................................. 2013-186194

(51) Int. Cl.
  *A61B 6/00*     (2006.01)
  *G01N 23/04*   (2006.01)
  *H04N 5/32*    (2006.01)

(52) U.S. Cl.
  CPC ........... *G01N 23/04* (2013.01); *A61B 6/4233* (2013.01); *A61B 6/4266* (2013.01); *A61B 6/4283* (2013.01); *A61B 6/4411* (2013.01); *A61B 6/467* (2013.01); *A61B 6/54* (2013.01); *A61B 6/548* (2013.01); *H04N 5/32* (2013.01); *A61B 6/465* (2013.01); *G01N 2223/3032* (2013.01); *G01N 2223/401* (2013.01)

(58) Field of Classification Search
  CPC ......... A61B 6/4266; A61B 6/465; A61B 6/54; A61B 6/548
  See application file for complete search history.

(56) References Cited

U.S. PATENT DOCUMENTS 5,602,889 A * 2/1997 Oldendorf ............ A61B 6/4464
                                                              378/195
7,154,994 B2 * 12/2006 Gray ..................... A61B 6/4233
                                                              250/370.09

(Continued)

FOREIGN PATENT DOCUMENTS

JP    2011-177348 A      9/2011
WO   WO 2006/095538 A1   9/2006
WO   WO 2012/008229 A1   1/2012

OTHER PUBLICATIONS

Foreign Office Action of JP 2013-186194 with English translation dated Sep. 9, 2015.

*Primary Examiner* — Thomas R Artman
(74) *Attorney, Agent, or Firm* — Birch, Stewart, Kolasch & Birch, LLP

(57) ABSTRACT

An X-ray imaging system includes a plurality of electronic cassettes having FPDs. One of the plural electronic cassettes for use in imaging is selected by input operation. Control is performed in a first mode operation being normal for the electronic cassette selected in the selecting step. Control is performed in a second mode operation being auxiliary of which driving power is lower than in the first mode operation for one of the electronic cassettes in an unselected state in the selecting step. Assuming that irradiation of the radiation is detected in the second mode operation, error information is displayed in relation to selecting the electronic cassette in the selecting step. For example, the first and second mode operations are pixel reset in which charge stored in pixels are swept in an FPD.

17 Claims, 23 Drawing Sheets

(56) References Cited

U.S. PATENT DOCUMENTS

| | | | |
|---|---|---|---|
| 7,239,685 B2* | 7/2007 | Petrick | G01T 1/2985 |
| | | | 378/116 |
| 7,483,515 B2* | 1/2009 | Nascetti | H04N 5/325 |
| | | | 250/370.09 |
| 7,778,390 B2* | 8/2010 | Schliermann | H05G 1/54 |
| | | | 378/115 |
| 7,819,581 B2* | 10/2010 | Srinivasan | G01T 7/005 |
| | | | 378/19 |
| 8,023,620 B2* | 9/2011 | Atzinger | A61B 6/467 |
| | | | 378/115 |
| 8,611,501 B2* | 12/2013 | Kobayashi | A61B 6/4405 |
| | | | 378/102 |
| 8,731,141 B2 | 5/2014 | Kuwabara | |
| 8,958,529 B2* | 2/2015 | Enomoto | H04N 5/32 |
| | | | 378/108 |
| 9,332,956 B2* | 5/2016 | Enomoto | H04N 5/32 |
| 2007/0165783 A1* | 7/2007 | Abu Tabanjeh | A61B 6/00 |
| | | | 378/116 |
| 2008/0118029 A1* | 5/2008 | Schliermann | H05G 1/54 |
| | | | 378/117 |
| 2011/0274251 A1* | 11/2011 | Omernick | G01T 7/00 |
| | | | 378/98.8 |
| 2012/0195407 A1* | 8/2012 | Nenoki | A61B 6/4283 |
| | | | 378/98.5 |
| 2015/0071414 A1* | 3/2015 | Oda | H04N 5/32 |
| | | | 378/207 |

* cited by examiner

F I G. 2

| OBJECT OF INTEREST | TUBE VOLTAGE | TUBE CURRENT | IRRADIATION TIME |
|---|---|---|---|
| ... | ... | ... | ... |
| CHEST | Va | Ia | Ta |
| ABDOMEN | Vb | Ib | Tb |
| ... | ... | ... | ... |

25

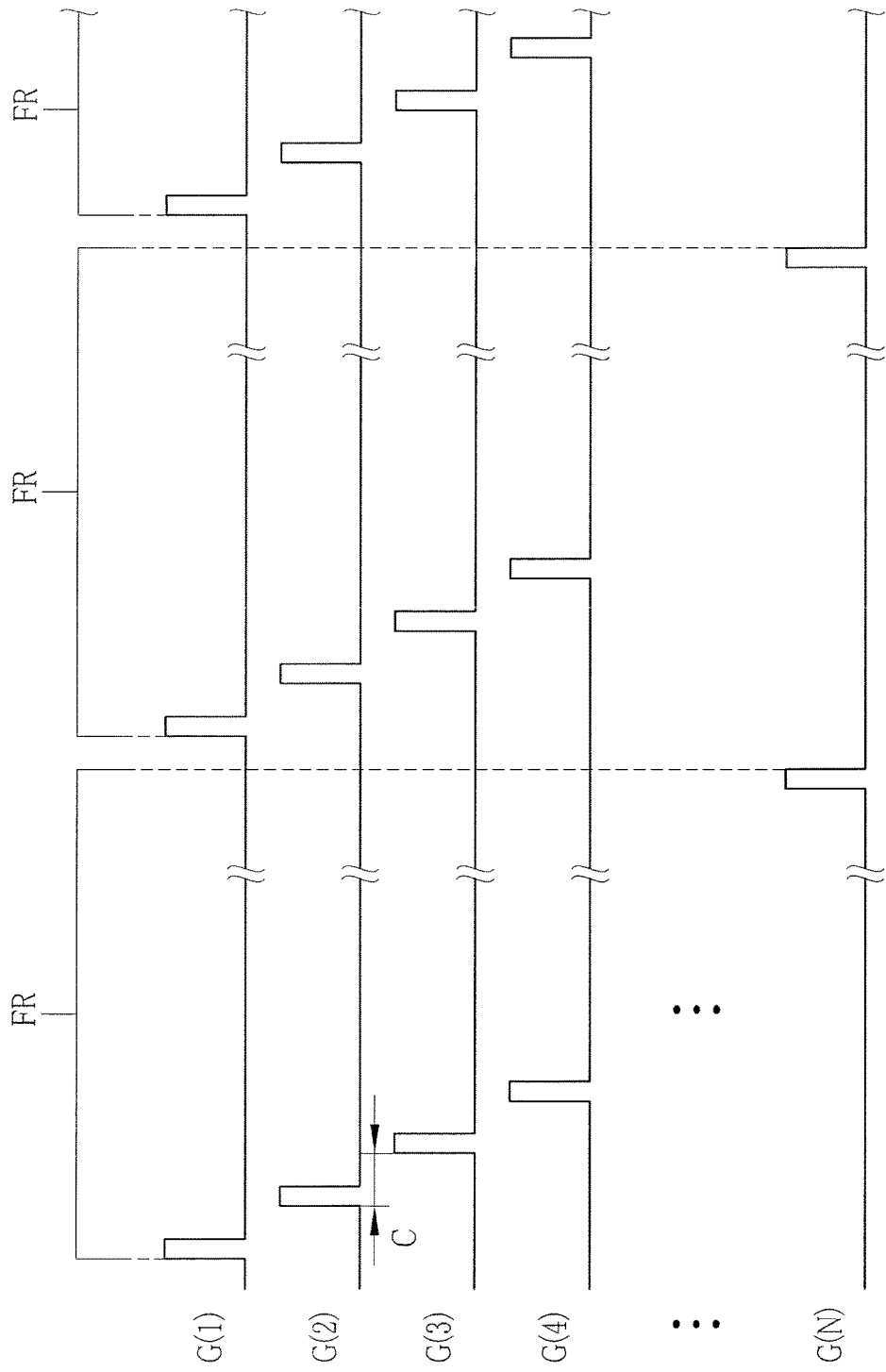

1ST MODE OPERATION

2ND MODE OPERATION

RADIOGRAPHIC IMAGING SYSTEM AND SYSTEM OPERATION METHOD

CROSS-REFERENCE TO RELATED APPLICATION

This application claims priority under 35 USC 119 from Japanese Patent Application No. 2013-186194, filed 9 Sep. 2013, the disclosure of which is incorporated by reference herein.

BACKGROUND OF THE INVENTION

1. Field of the Invention

The present invention relates to a radiographic imaging system and system operation method. More particularly, the present invention relates to a radiographic imaging system and system operation method, in which selection of one of plural radiographic image detectors can be checked for correct use without an error.

2. Description Related to the Prior Art

An X-ray imaging system or radiographic imaging system is well-known in the field of medical diagnosis. The X-ray imaging system includes an X-ray source apparatus or radiation source apparatus, and an X-ray imaging apparatus or radiographic imaging apparatus. The X-ray source apparatus generates X-rays. The X-ray imaging apparatus forms an X-ray image. The X-ray source apparatus includes an X-ray source or radiation source, and a source driver (controllable) or source control unit. The X-ray source applies X-rays to a body of a patient. The source driver drives the X-ray source. The X-ray imaging apparatus includes electronic cassettes or radiographic image detectors, an imaging control unit and a console unit or user interface device. The electronic cassettes detect the X-ray image by receiving X-rays transmitted through the body. The imaging control unit controls the electronic cassettes. The console unit stores and displays the X-ray image.

The electronic cassette includes a sensor panel and a control circuit board. The sensor panel is a flat panel detector (FPD) for detecting the X-ray image as an electric signal. Numerous pixels are arranged on the sensor panel two-dimensionally for storing signal charge in response to X-rays. The control circuit board includes a gate driver, signal processor, and controller. The gate driver reads out the signal charge from the pixels per unit of pixel rows. The signal processor converts the signal charge into an image signal constituting the X-ray image. The controller controls the sensor panel in connection with the gate driver and the signal processor.

A plurality of the electronic cassettes are frequently prepared and used in combination even in an examination room, for various purposes, such as erect posture and supine posture. For X-ray imaging, the body is positioned in a suitable manner. One of the electronic cassettes for imaging among the electronic cassettes is selected by a physician or operator at the console unit, for example, radiologist or technician. In the field of diagnosis, there is risk of mistaking the electronic cassettes due to the operator. A second one of the electronic cassettes (where the body is not positioned) different from a first one of the electronic cassettes (where the body is positioned) may be selected manually. As a result, the X-ray image in which no object of interest in the body is imaged may be formed. To solve this problem, U.S. Pat. No. 8,731,141 (corresponding to JP-A 2011-177348) discloses improvement of the X-ray imaging system.

In U.S. Pat. No. 8,731,141, all the electronic cassettes operable for selection at the console unit are driven for detecting the X-ray image irrespective of selection of an operator. A number of the X-ray images are formed by the electronic cassettes, and automatically refined to select candidate images with an object, or manually selected by the operator. Should the candidate images be derived from an unselected one of the electronic cassettes, then an alarm signal is generated, for example, alarm sound from a loudspeaker, alarm message on a display panel of the console unit, to inform the operator of his or her error in the selection of the electronic cassettes.

In the X-ray imaging system of U.S. Pat. No. 8,731,141, the X-ray image of the purpose can be formed reliably even in occurrence of an error in the selection of the operator. However, all the electronic cassettes controllable with the console unit are driven for detecting the X-ray image. There occurs wasteful use of electric power for a second one of the electronic cassettes other than a first one of the electronic cassettes outputting the X-ray image of the purpose.

In a type of the electronic cassettes, an internal battery is contained for power supply. The electronic cassettes are wirelessly connected with the imaging control unit or other apparatuses. The use of the method of U.S. Pat. No. 8,731,141 in the electronic cassettes may cause a problem in that the battery is quickly consumed because considerably high power is used. The battery must be recharged frequently even while the electronic cassettes are not used for imaging.

SUMMARY OF THE INVENTION

In view of the foregoing problems, an object of the present invention is to provide a radiographic imaging system and system operation method, in which selection of one of plural radiographic image detectors can be checked for correct use without an error.

In order to achieve the above and other objects and advantages of this invention, a radiographic imaging system includes a plurality of radiographic image detectors each of which has a sensor panel for detecting a radiographic image according to radiation, and a user input interface for selecting one of the plural radiographic image detectors for use in imaging. The radiographic imaging system includes a controller, associated with each of the radiographic image detectors, for performing a first mode operation for the radiographic image detector in case a selected state is set according to the user input interface, and performing a second mode operation for the radiographic image detector in case an unselected state is set according to the user input interface, where driving power in the second mode operation is lower than in the first mode operation for detecting irradiation of the radiation. A display device for, assuming that irradiation of the radiation is detected in the second mode operation, displays error information in relation to selecting the radiographic image detector with the user input interface.

Preferably, the user input interface selectively generates a selection signal of the selected state of the radiographic image detector and a non-selection signal of the unselected state of the radiographic image detector. Each of the radiographic image detectors has a communication interface for receiving the selection signal and the non-selection signal. The controller selects the first mode operation upon receiving the selection signal, and selects the second mode operation upon receiving the non-selection signal.

Preferably, before the communication interface receives the selection or non-selection signal, powering of the sensor panel is turned off, and in case the communication interface receives the selection or non-selection signal, the sensor panel starts being powered to start the first or second mode operation.

Preferably, the radiographic image detector is wirelessly on-line with a related apparatus by use of the communication interface, and is supplied with power by a battery.

Preferably, the first mode operation is detection of a start of irradiation of the radiation.

Preferably, the sensor panel includes a panel device having pixels arranged two-dimensionally for storing signal charge upon receiving the radiation, and a signal processor for converting the signal charge into an image signal to generate the radiographic image. At least one of the first and second mode operations includes pixel reset in which charge stored in the pixels is swept in the panel device. The radiographic image detector includes a level detection device for detecting irradiation of the radiation according to the charge swept in the pixel reset.

Preferably, the signal processor converts the charge swept in the pixel reset into a dose signal of a dose of the radiation reaching the panel device, and transmits the dose signal to the level detection device.

Preferably, the first mode operation is sequential reset of a method of pixel reset in which charge of the pixels is swept by one pixel row from a first pixel row to a final pixel row in the sensor panel, and the charge of one frame is swept by sweeping the charge of the final pixel row so as to repeat sweep of the charge by returning to the first pixel row.

Preferably, the second mode operation is the sequential reset of the method of the pixel reset in the sensor panel.

Preferably, the sequential reset of the method of the pixel reset for one frame is performed at a longer interval in the second mode operation than in the first mode operation.

In one preferred embodiment, the sequential reset of the method of the pixel reset for one pixel row is performed at a longer interval in the second mode operation than in the first mode operation.

In still another preferred embodiment, the second mode operation is pixel binning of a method of pixel reset in which the charge of pixels of plural adjacent pixel rows are swept together in the sensor panel.

In one preferred embodiment, the second mode operation is selective reset of a method of pixel reset in which the charge stored in the pixels of particular pixel rows are selectively swept in the sensor panel.

Preferably, furthermore, an artifact corrector estimates a lag value of next imaging according to lag value information of a relationship between a lag value from residual charge in the pixels in preceding imaging and elapsed time from the preceding imaging, and for correcting the radiographic image in artifact correction of image lag according to the estimated lag value.

Preferably, assuming that irradiation of the radiation is detected in the second mode operation, the artifact corrector updates the lag value information in consideration of the lag value upon detection, to use the updated lag value information for the artifact correction of image lag.

Preferably, the artifact corrector updates the lag value information according to first and second time points. The first time point is a time point where irradiation of the radiation in the second mode operation is detected by a first radiographic image detector unselected according to the user input interface among the plural radiographic image detectors. The second time point is later than the first time point, and is a time point where irradiation of the radiation in the first mode operation is detected by the first radiographic image detector for next imaging upon selecting the first radiographic image detector according to the user input interface.

Also, a system operation method for a plurality of radiographic image detectors for detecting a radiographic image is provided, and includes a step of selecting one of the plural radiographic image detectors for use in imaging by input operation. A first mode operation is performed for the radiographic image detector selected in the selected step. A second mode operation is performed for one of the radiographic image detectors unselected in the selecting step, where driving power in the second mode operation is lower than in the first mode operation for detecting irradiation of the radiation. Assuming that irradiation of the radiation is detected in the second mode operation, error information is displayed in relation to selecting the radiographic image detector in the selecting step.

Consequently, selection of one of plural radiographic image detectors can be checked for correct use without an error, because checking with first and second mode operations is effective for detecting an error in the selection.

BRIEF DESCRIPTION OF THE DRAWINGS

The above objects and advantages of the present invention will become more apparent from the following detailed description when read in connection with the accompanying drawings, in which:

FIG. 2 is a table illustrating a parameter table for conditions;

FIG. 12 is a timing chart illustrating a state of generating a gate pulse in the first mode operation;

DETAILED DESCRIPTION OF THE PREFERRED EMBODIMENT(S) OF THE PRESENT INVENTION

First Preferred Embodiment

Figure 1:
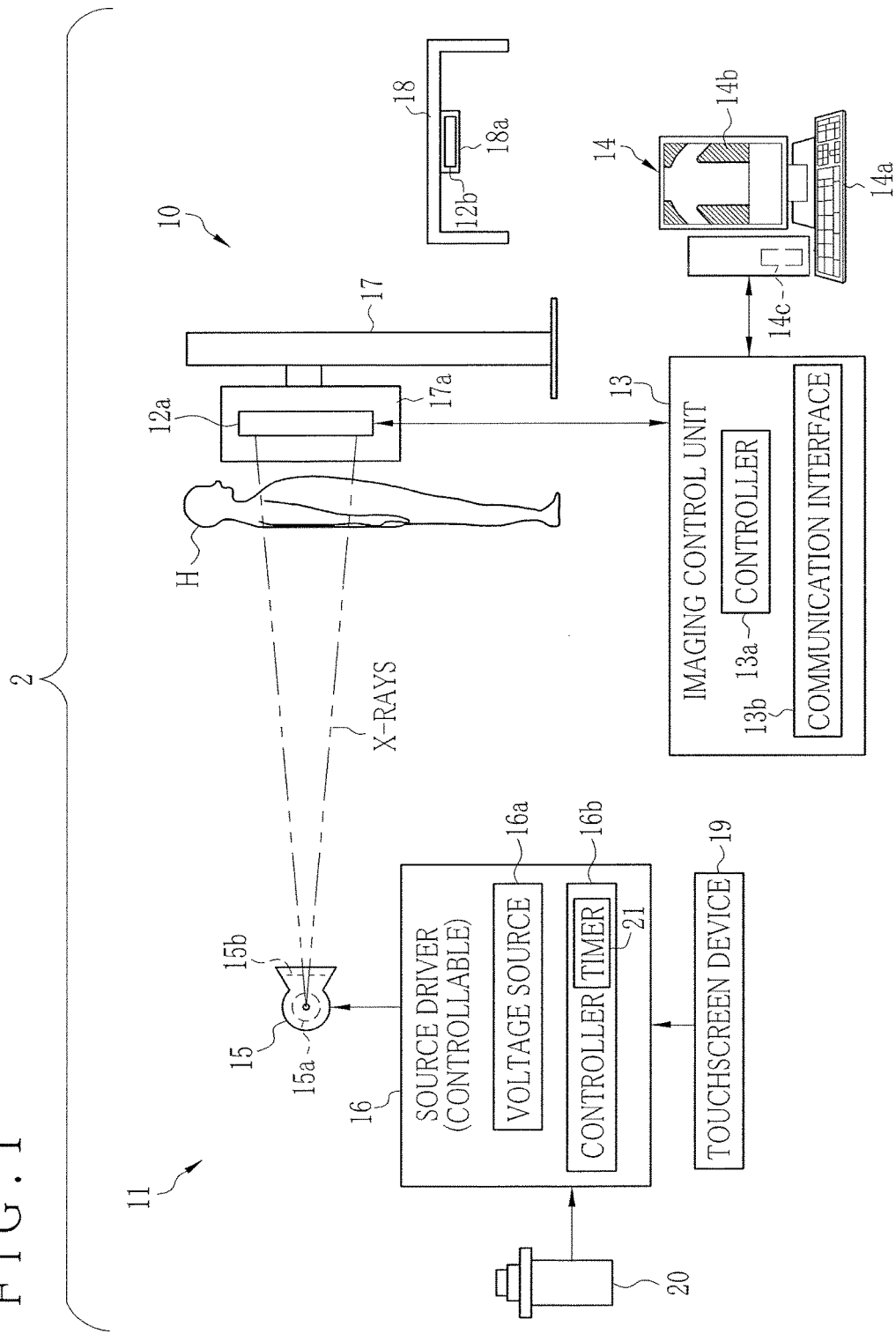
FIG. 1 is a block diagram schematically illustrating an X-ray imaging system.

In FIG. 1, an X-ray imaging system 2 or radiographic imaging system includes an X-ray imaging apparatus 10 or radiographic imaging apparatus, and an X-ray source apparatus 11 or radiation source apparatus. The X-ray imaging apparatus 10 is constituted by two electronic cassettes 12a and 12b or radiographic image detectors, an imaging control unit 13 and a console unit 14 or user interface device. The electronic cassettes 12a and 12b are portable, detect X-rays transmitted through a body H of a patient, and output X-ray images. The imaging control unit 13 controls detection of the electronic cassettes 12a and 12b. The console unit 14 includes a storage for storing X-ray images and performs display control of those. The X-ray source apparatus 11 includes an X-ray source 15 or radiation source, and a source driver 16 (controllable) or source control unit. The X-ray source 15 applies X-rays to the body H. The source driver 16 powers and controls the X-ray source 15.

The X-ray imaging apparatus 10 is not connected with the X-ray source apparatus 11 electrically. There is no sync signal between the X-ray imaging apparatus 10 and the X-ray source apparatus 11 for synchronizing the X-ray imaging apparatus 10 and the X-ray source apparatus 11. However, each of the electronic cassettes 12a and 12b includes a detecting function for detecting a start of irradiating X-rays, so that the time points of actuation of the electronic cassettes 12a and 12b can be synchronized with a time point of starting irradiation of X-rays from the X-ray source apparatus 11.

A floor stand 17 for radiography is used for imaging of the body H in an erect orientation. A cassette holder 17a is incorporated in the floor stand 17, and receives the electronic cassette 12a in a removable manner. An imaging table 18 for radiography is used for imaging of the body H in a supine posture. A cassette holder 18a is incorporated in the imaging table 18, and receives the electronic cassette 12b in a removable manner. In FIG. 1, the electronic cassette 12a is set on the cassette holder 17a. The electronic cassette 12b is set on the cassette holder 18a. Only the electronic cassette 12a is used for X-ray imaging. It is also possible to set the electronic cassette 12a on the cassette holder 18a of the imaging table 18 and set the electronic cassette 12b on the cassette holder 17a of the floor stand 17 in a state reverse to the state of FIG. 1. Note that the electronic cassette 12b is structurally the same as the electronic cassette 12a. Those are hereinafter referred to as an electronic cassette 12 or radiographic image detector, on the condition without requiring distinction.

A front wall 34a of the electronic cassette 12 (See FIG. 5) is oriented to the X-ray source 15 to mount the electronic cassette 12 on the cassette holder 17a or 18a of the floor stand 17 and the imaging table 18. The body H is positioned by a physician or operator to dispose an object of interest (body part) between the X-ray source 15 and the electronic cassette 12. A moving mechanism (not shown) moves the X-ray source 15 in various directions and positions. The X-ray source 15 is commonly used between the floor stand 17 and the imaging table 18. Note that two of the X-ray source 15 can be disposed for respectively the floor stand 17 and the imaging table 18.

The console unit 14 includes a user input interface 14a with a keyboard, a display panel 14b, a storage medium 14c or hard disk (HDD), and the like. The user input interface 14a is manipulated by the operator to input various control signals, for example, imaging condition. Also, the control signals include information of the electronic cassette 12 for use among the electronic cassettes 12a and 12b. The console unit 14 is operable for receiving inputs.

The display panel 14b displays an X-ray image detected by the electronic cassette 12, and an input screen for the imaging condition, and the like. An example of the storage medium 14c is a hard disk drive for storing X-ray images from the electronic cassette 12 and various data required for X-ray imaging. Note that the X-ray images can be stored in an image storage server (not shown) communicable with the console unit 14 by network connection.

The storage medium 14c stores ID information of the electronic cassettes 12a and 12b. To input the ID information, an operator manually inputs the ID information with the user input interface 14a after purchasing the electronic cassettes 12a and 12b. Otherwise, a reader (not shown) reads a bar code or RFID tag on the electronic cassettes 12a and 12b for inputting the ID information. The console unit 14 recognizes the ID information to determine which of the electronic cassettes 12a and 12b is the electronic cassette 12 for use in the user input interface 14a for imaging.

Information of an imaging request is received by the console unit 14, and displayed on the display panel 14b. The information of the imaging request includes the sex, age and body part or object of interest, examples of the body part including a head, chest, abdomen, hand, fingers and the like. An external information system (not shown) inputs the imaging request, such as the Hospital Information System (HIS) and Radiology Information System (RIS) for managing object information and diagnosis information in relation to the radiographic imaging. It is also possible for an operator manually to input the imaging request by use of the user input interface 14a.

The X-ray source 15 includes an X-ray tube 15a and a collimator 15b. The X-ray tube 15a emits X-rays. The collimator 15b limits a path of irradiation to the body H downstream of the X-ray tube 15a. Various elements are associated with the X-ray tube 15a, including a filament, target and a grid electrode (all not shown). Tube voltage is applied to a portion between the filament as cathode and the target as anode. The filament generates thermal electron according to the tube voltage. The thermal electron is emitted toward the target. The target emits X-rays by collision of the thermal electron from the filament. The grid electrode is disposed between the filament and the target, and changes a flow of the thermal electron (tube current) from the filament to the target according to the applied voltage.

The collimator 15b is constituted by four plates of metal lead arranged quadrilaterally for blocking X-rays. An emission opening of a quadrilateral shape is defined in the collimator 15b at the center for transmitting X-rays. Positions of the plates are changed to change the size of the emission opening, to change a field of emission of X-rays.

The source driver 16 includes a voltage source 16a and a controller 16b. The voltage source 16a generates a tube voltage and voltage for application to a grid electrode. The controller 16b controls operation of the voltage source 16a to adjust the tube voltage, tube current and irradiation time of X-rays. A touchscreen device 19 or touchscreen panel and a start switch 20 for irradiation are connected to the source driver 16. The touchscreen device 19 is manually operable by an operator for inputting an irradiation condition of X-rays. The start switch 20 is operable for starting warmup of the X-ray source 15 and starting irradiation of X-rays.

An irradiation condition input by use of the touchscreen device 19 includes the tube voltage, tube current and irradiation time of X-rays. A memory (not shown) is incorporated in the controller 16b, and stores a plurality of preset irradiation conditions, for example, for the chest, head and the like. The controller 16b reads the preset irradiation conditions, and causes the touchscreen device 19 to display the irradiation conditions in a form of icons, tabs or the like. The operator views the touchscreen device 19 and selects and confirms his or her desired one of the irradiation conditions. It is possible finely to adjust the irradiation conditions being input. The controller 16b operates in compliance with the irradiation condition from the touchscreen device 19, and controls various values including the tube voltage generated by the voltage source 16a, voltage applied to the grid electrode, and time for applying the tube voltage, namely the irradiation time of X-rays.

The start switch 20 is a button of a two-step type. The start switch 20, upon being depressed halfway at a first step, generates a warmup signal, and upon being depressed fully at a second step, generates a start signal for irradiation. Those signals are input to the controller 16b.

In case the warmup signal is input, the controller 16b causes the voltage source 16a to start warming up the X-ray source 15. To this end, the voltage source 16a applies a predetermined voltage to the filament for preheating, and rotates the target simultaneously. A limited voltage is applied to the grid electrode at such a level that thermal electron from the filament does not reach the target and does not cause irradiation of X-rays. After the preheating of the filament, the warmup is terminated in case the target comes to rotate at a predetermined rotational speed.

Upon inputting the start signal, the controller 16b operates the voltage source 16a to start the X-ray source 15 irradiating X-rays. Specifically, the tube voltage determined by the irradiation condition is applied to the target. Then voltage according to the tube current of the irradiation condition is applied to the grid electrode.

A timer 21 is incorporated in the controller 16b and starts measuring time upon the start of irradiating X-rays. In case the time measured by the timer 21 becomes equal to the predetermined irradiation time, the controller 16b causes the voltage source 16a to stop the X-ray source 15 from emitting X-rays. To this end, the voltage applied to the grid electrode is changed over to the warmup voltage. Then voltage to the target is turned off. Finally, voltage to the filament is turned off. Also, the controller 16b operates assuming that the measured time becomes equal to a maximum irradiation time predetermined in the source driver 16 for the fail-safe purpose, and causes the voltage source 16a to stop irradiation of X-rays in the same manner as in case the time measured by the timer 21 becomes equal to the predetermined irradiation time.

The imaging control unit 13 includes a controller 13a and a communication interface 13b. The communication interface 13b transmits and receives information between the electronic cassette 12 and the console unit 14. Examples of the information between the electronic cassette 12 and the console unit 14 are information of X-ray images, imaging conditions, and a selection signal and non-selection signal. See FIGS. 3 and 4.

In FIG. 2, a parameter table 25 for conditions is stored in the storage medium 14c of the console unit 14. Information in the parameter table 25 includes body information of the body H and the irradiation condition of X-rays from the X-ray source 15. Examples of the body information include information of an object of interest (body part), and sex, age and body thickness of the body H. In FIG. 2, only the object of interest is illustrated. The irradiation condition includes information of the tube voltage, tube current and irradiation time of X-rays, and is determined by considering information of the object of interest and the body H.

The parameter table 25 is information of a relationship between body parts (objects of interest), such as chest and abdomen, and imaging conditions. Incase an operator selects one of the body parts by use of the user input interface 14a, one of the imaging conditions is read out and displayed on the display panel 14b. It is also possible finely to adjust the values of the imaging conditions from the parameter table 25 according to information of the body H, such as sex, age, body thickness and the like. The operator views an imaging request on the display panel 14b, and manipulates the user input interface 14a for inputting the imaging condition according to the imaging request. Information of the determined imaging condition is transmitted from the console unit 14 to the imaging control unit 13, and from the imaging control unit 13 to the electronic cassette 12. The same imaging condition input to the console unit 14 is set in the source driver 16 by the operator with the touchscreen device 19. Note that discrete data of the tube current and irradiation time are included in the information in the parameter table 25. However, a current-time product (mAs) can be recorded as a result of multiplication of the tube current and the irradiation time, because a total dose of the X-rays is determined by the product of the tube current and the irradiation time.

Figure 3:
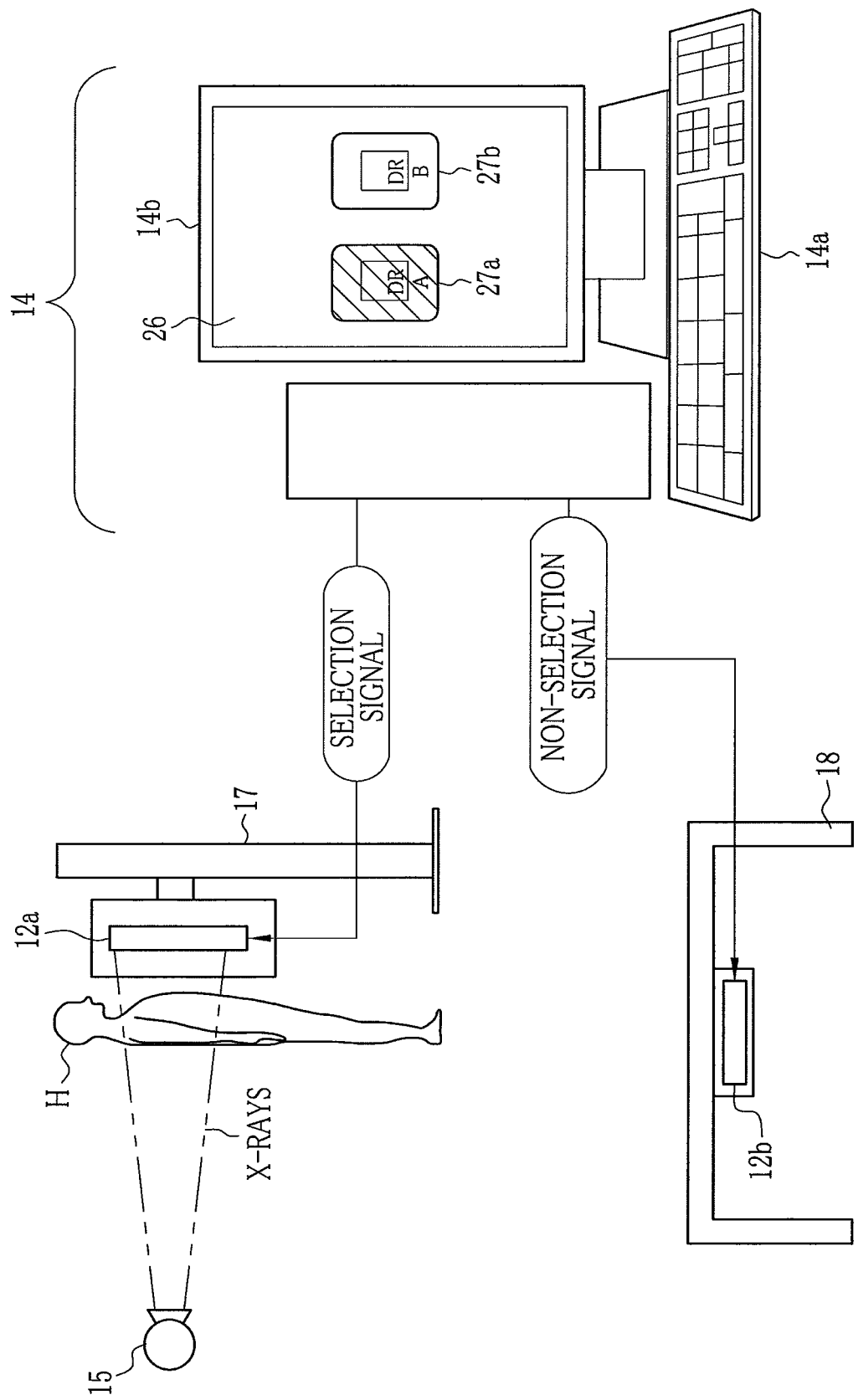
FIG. 3 is an explanatory view illustrating selection of an electronic cassette.
Figure 4:
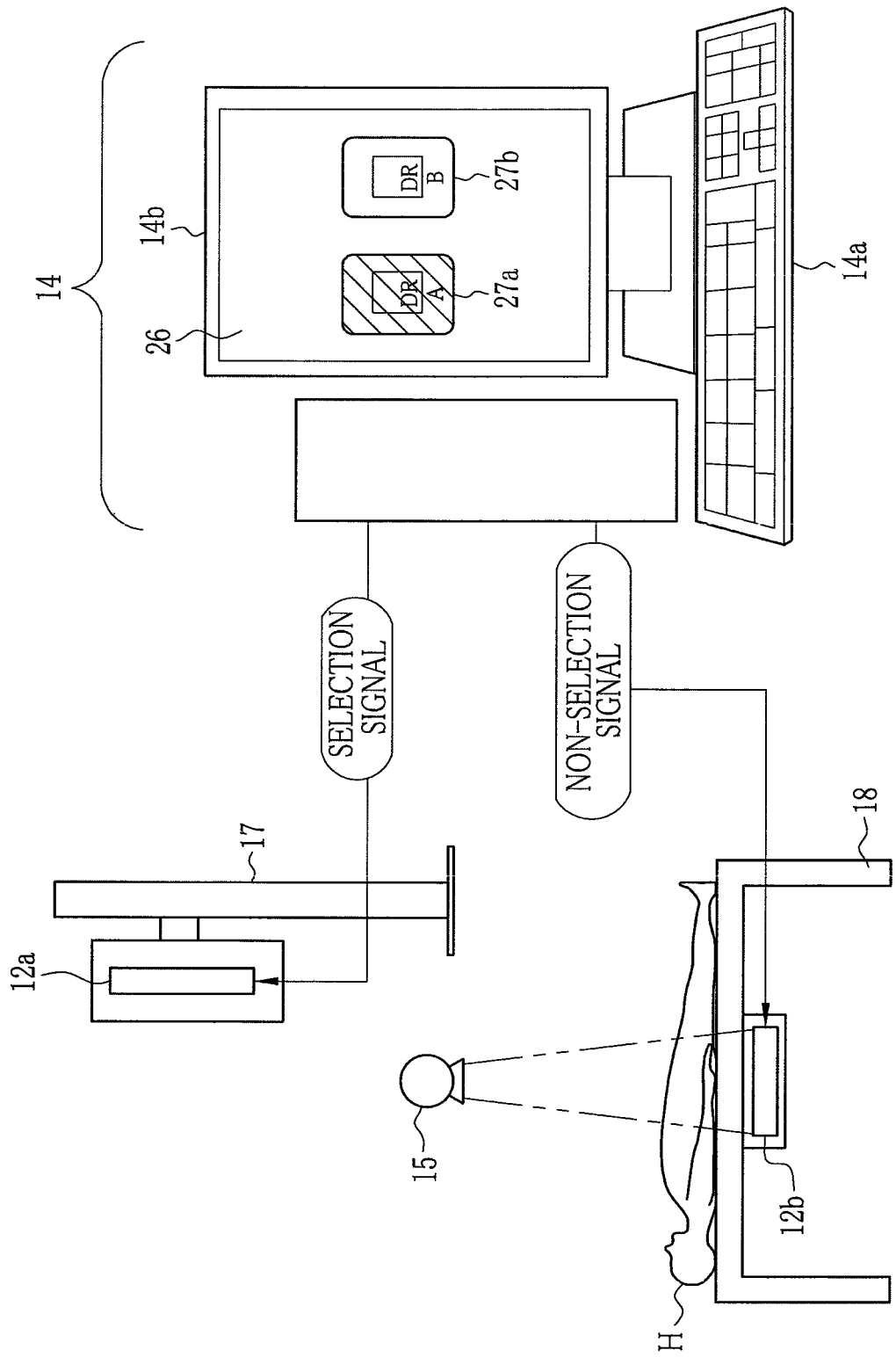
FIG. 4 is an explanatory view illustrating erroneous selection of an electronic cassette.

In FIGS. 3 and 4, a selection screen 26 is displayed on the display panel 14b for selecting the electronic cassette 12 from the electronic cassettes 12a and 12b for the purpose of imaging. The selection screen 26 has a first icon 27a for the electronic cassette 12a and a second icon 27b for the electronic cassette 12b. The icons 27a and 27b are always selected exclusively, as selection of one of those is canceled automatically in response to selection of a remaining one of them. In each of FIGS. 3 and 4, the first icon 27a is selected as hatched.

The console unit 14 sends a selection signal to one of the electronic cassettes 12a and 12b as information of being selected for use in the imaging. The console unit 14 sends a non-selection signal to a remaining one of the electronic cassettes 12a and 12b as information of not being selected for use. In the description below, the electronic cassette 12 being selected is referred to a selected cassette. The electronic cassette 12 being not selected is referred to an unselected cassette. In FIGS. 3 and 4, the first icon 27*a* is specified. The electronic cassette 12*a* is the selected cassette. The electronic cassette 12*b* is the unselected cassette. The selection signal is sent to the electronic cassette 12*a*. The non-selection signal is sent to the electronic cassette 12*b*.

In FIG. 3, the electronic cassette 12*a* as selected cassette operates for imaging. The electronic cassette 12 selected with the selection screen 26 for imaging now coincides with the electronic cassette 12 receiving X-rays. Namely, the selection of the electronic cassette 12 with the selection screen 26 is correct or proper. In FIG. 4, the electronic cassette 12*b* as unselected cassette operates for imaging. The electronic cassette 12 selected with the selection screen 26 for imaging is different from the electronic cassette 12 receiving X-rays. Namely, the selection of the electronic cassette 12 with the selection screen 26 is incorrect or improper. The reason for this error is that the operator has not selected the second icon 27*b* which should have been selected with the selection screen 26, or has selected the first icon 27*a* erroneously.

Figure 5:
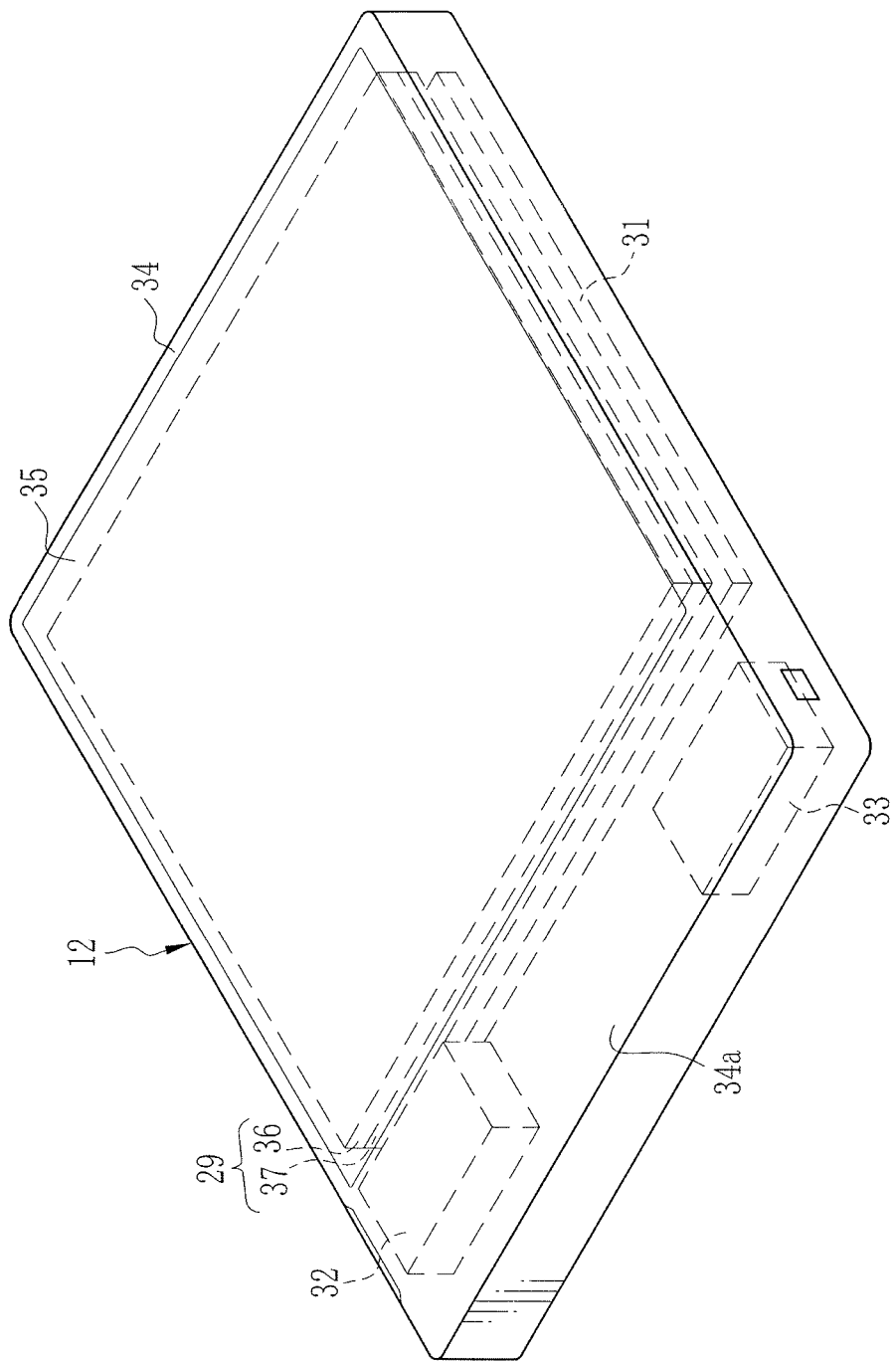
FIG. 5 is a perspective view illustrating the electronic cassette.

In FIG. 5, the electronic cassette 12 includes a panel device 29, a control circuit board 31, a communication interface 33 and a portable housing 34 for containing the various elements. The electronic cassette 12 is loaded with a battery 32. The portable housing 34 is formed from electrically conductive resin. A quadrilateral opening is formed in the front wall 34*a* of the portable housing 34 for receiving X-rays. A radio-transparent plate 35 is fitted in the opening as a top plate. The radio-transparent plate 35 is formed from carbon material, which is lightweight, highly rigid, and radio-transparent to X-rays.

The portable housing 34 is in a size defined according to the international standards ISO 4090:2001 for the film cassette and IP cassette. The portable housing 34 can be mounted on a well-known type of floor stand of imaging for the film cassette and IP cassette. Also, the electronic cassette 12 can be placed on a table where the body H lies, or manually held by a patient of the body H for use without setting on the floor stand.

A power supply circuit (not shown) is connected with the battery 32, and caused to supply elements of the electronic cassette 12 with power. The battery 32 is removable from the portable housing 34. A special charger (not shown) is used to charge the battery 32 electrically. The communication interface 33 is wirelessly on-line with the imaging control unit 13, and transmits and receives information of various types with the imaging control unit 13, the information including the imaging conditions, X-ray images and the like. Also, the communication interface 33 receives a selection signal or non-selection signal from the console unit 14 through the imaging control unit 13. There is a controller 54 to which the communication interface 33 outputs received information. A memory 52 stores the X-ray images after correction. The communication interface 33 receives the X-ray image from the memory 52 through the controller 54, and transmits those to the console unit 14.

The panel device 29 is constituted by a scintillator 36 and a light receiving unit 37 or detection board. The light receiving unit 37 is disposed downstream of the scintillator 36 according to an optical path of X-rays in a layered structure. The scintillator 36 includes phosphor, such as thallium activated cesium iodide (CsI:Tl), and GOS or terbium activated gadolinium oxysulfide ($Gd_2O_2S$:Tb), and converts X-rays from the radio-transparent plate 35 into visible light.

The light receiving unit 37 detects visible light emitted by the scintillator 36 and converts the light into an electric signal. The control circuit board 31 controls the light receiving unit 37, and generates an X-ray image according to the electric signal from the light receiving unit 37.

Figure 6:
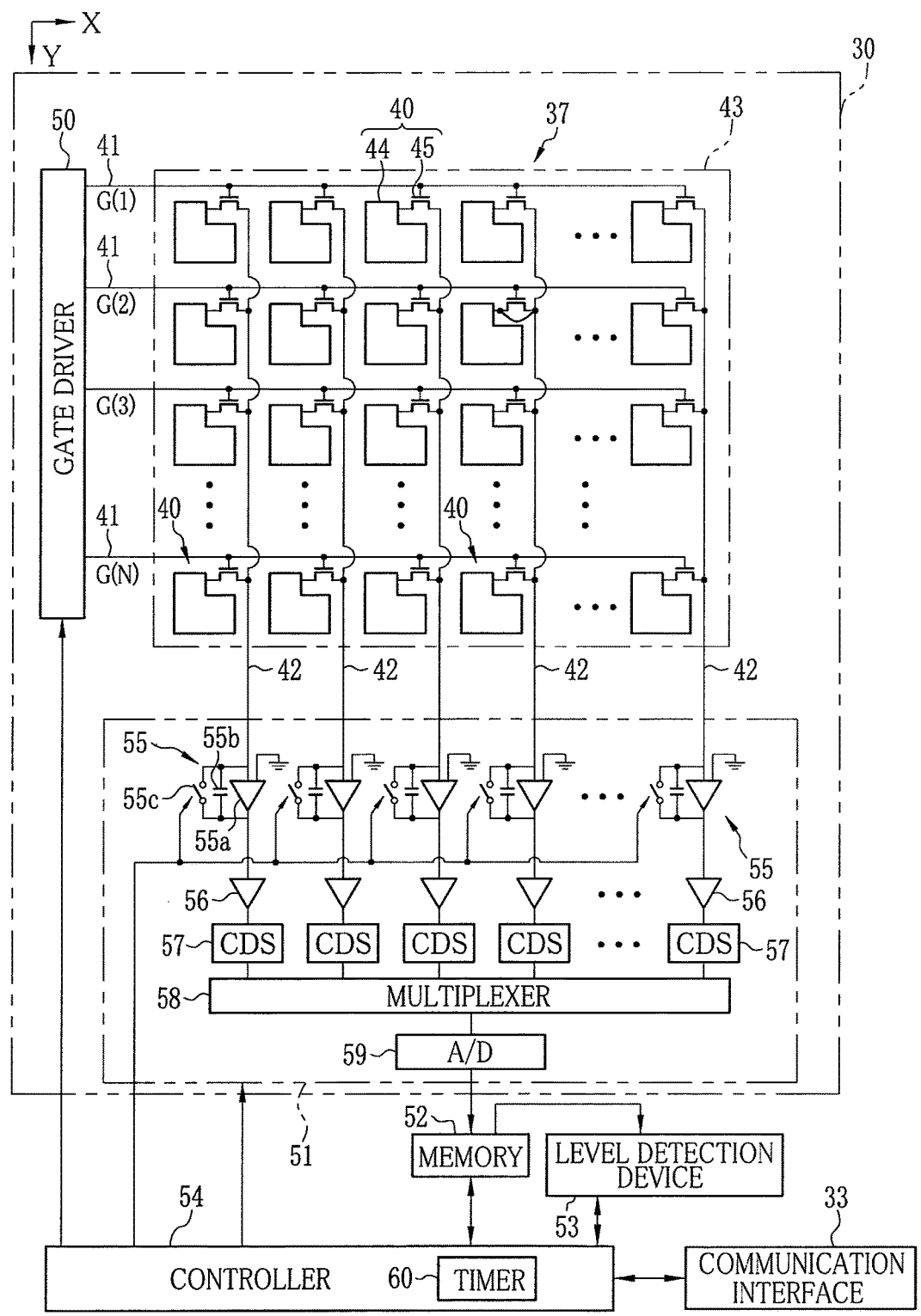
FIG. 6 is a block diagram schematically illustrating circuit elements in the electronic cassette.

In FIG. 6, the light receiving unit 37 includes a glass substrate (not shown), pixels 40, N scan lines 41, and M signal lines 42. The pixels 40 are arranged in a matrix two-dimensionally in N rows and M columns. The scan lines 41 extend in the X direction or row direction of the pixels 40, and are arranged at a regular pitch in the Y direction or columnar direction of the pixels 40. The signal lines 42 extend in the Y direction, and are arranged at a regular pitch in the X direction. The signal lines 42 are perpendicular to the scan lines 41. The pixels 40 are positioned at intersections between the scan lines 41 and the signal lines 42. An active pixel area 43 is defined by an area on the glass substrate having the pixels 40. N and M are integers equal to or more than 2, for example, both approximately 2,000. The position of the pixels 40 is expressed by the X and Y-coordinates with reference to the origin (0, 0) at an upper left corner pixel among the pixels 40. Note that the arrangement of the pixels 40 can be a honeycomb arrangement instead of the rectangular arrangement of the present embodiment.

Each of the pixels 40 includes a photoconductive element 44 and a thin film transistor 45 (TFT). The photoconductive element 44 generates charge (electron/hole pair) upon entry of visible light and stores the charge. The thin film transistor 45 is a switching element. The photoconductive element 44 includes a semiconductor layer for generating charge, and upper and lower electrodes between which the semiconductor layer is disposed. The semiconductor layer is a PIN type (p-intrinsic-n type). The n type layer is formed with the upper electrode. The p type layer is formed with the lower electrode. In the thin film transistor 45, a gate electrode is connected to the scan lines 41. A source electrode is connected to the signal lines 42. A drain electrode is connected to the lower electrode of the photoconductive element 44.

One of the bias lines (not shown) is connected to the upper electrode of the photoconductive element 44. The number of the bias lines is N or the number of the pixel rows of the pixels 40. Those are connected to a single bus line. The bus line is connected to a bias power source. The bias power source applies a positive bias voltage to the upper electrode of the photoconductive element 44 through the bus line and the bias line as subsidiaries. An electric field is created in the semiconductor layer by application of the positive bias voltage. The photoconductive element 44 is used in a reversely biased state. An electron-hole pair is created in the semiconductor layer by the photoelectric conversion. An electron moves to the upper electrode and is absorbed in the bias lines. The positive hole moves to the lower electrode and is collected as signal charge.

The control circuit board 31 includes a gate driver 50, a signal processor 51, the memory 52, a level detection device 53 and the controller 54. The gate driver 50 is connected to each of ends of the scan lines 41, and generates gate pulses G(K) for driving the thin film transistors 45, where K is from 1 to N. See FIG. 9. The controller 54 causes a sensor panel 30 to operate for the pixel reset and the image readout. In the pixel reset, the sensor panel 30 causes the gate driver 50 to drive the thin film transistors 45 and resets the pixels 40 by reading out the dark current charge. In the image readout, the sensor panel 30 reads out the signal charge from the pixels 40.

The signal processor 51 is connected to each of the ends of the signal lines 42. The signal processor 51 includes integrating amplifiers 55, gain amplifiers 56, correlated double samplers 57 (CDS), a multiplexer 58 and an A/D converter 59.

The integrating amplifiers 55 are associated with respectively the signal lines 42. Each of the integrating amplifiers 55 includes an operational amplifier 55a, a capacitor 55b and an amplifier reset switch 55c. The operational amplifier 55a has two inputs and one output. A first one of the inputs is connected with one of the signal lines 42. A second one of the inputs is grounded by use of a ground line. The capacitor 55b and the amplifier reset switch 55c are connected between the first input and the output in parallel with one another.

The integrating amplifiers 55 accumulate the signal charge from the signal lines 42 by storing in the capacitor 55b, and output a voltage value (signal voltage) of an analog form according to the cumulative value. The amplifier reset switch 55c is driven and controlled by the controller 54. Turning on the amplifier reset switch 55c resets (abandons) the signal charge stored in the capacitor 55b.

The gain amplifier 56 is connected to an output terminal of the operational amplifier 55a, and amplifies a signal voltage output by the integrating amplifiers 55 at a predetermined gain value. The gain value is determined by the controller 54 according to an imaging condition from the console unit 14.

The correlated double sampler 57 is connected to an output terminal of the gain amplifier 56, and processes the signal voltage amplified by the gain amplifier 56 for correlated double sampling well-known technically, and eliminates reset noise of the integrating amplifier 55 from the signal voltage. To be precise, the correlated double sampler 57 includes two sample-hold circuits and one differential circuit (all not shown). A first one of the sample-hold circuits samples and holds the signal voltage output by the gain amplifier 56. A second one of the sample-hold circuits samples and holds a component of reset noise of the integrating amplifier 55 output by the gain amplifier 56 upon resetting the integrating amplifier 55. The differential circuit determines a difference between the signal voltage and the reset noise component, to acquire a signal voltage after eliminating the noise.

The multiplexer 58 is connected to an output of each of the correlated double samplers 57, and selects the correlated double samplers 57 by one column from a first column to an Mth column, and inputs a signal voltage from the correlated double samplers 57 to the A/D converter 59 serially. The A/D converter 59 converts the input signal voltage by A/D conversion, and outputs the digital signal voltage. The memory 52 stores the digital signal voltage from the A/D converter 59 as an X-ray image.

The level detection device 53 is controlled by the controller 54. The level detection device 53 carries out start detection in which a start of irradiation of X-rays is detected, and carries out irradiation detection in which the irradiation is detected.

In the embodiment, the sensor panel 30 or flat panel detector (FPD) is defined to include the panel device 29, the gate driver 50 and the signal processor 51.

A timer 60 is incorporated in the controller 54. Irradiation time of target is set in the timer 60 according to the imaging condition input with the console unit 14. In case the level detection device 53 detects a start of irradiation of X-rays, the timer 60 starts measuring elapsed time. The controller 54 detects a stop of the irradiation in case the measured elapsed time in the timer 60 becomes equal to the irradiation time.

The controller 54 includes various correction devices (not shown) for correcting an X-ray image stored in the memory 52 for various functions, including offset correction, sensitivity correction, defect correction and the like. Among those, an offset correction device subtracts an offset correction image from an X-ray image per unit of the pixel so as to eliminate constant patterned noise from the X-ray image due to specificity or imaging environment of the signal processor 51, the offset correction image being acquired by the image readout without irradiation of X-rays. A sensitivity correction device (gain corrector) corrects unevenness in the sensitivity of the photoconductive element 44 of the pixels 40 and unevenness in the output characteristic of the signal processor 51. A defect correction device operates according to defective pixel information created preliminarily at the time of shipment or periodic maintenance, and linearly interpolates pixel values of the defective pixels according to those of normal pixels disposed around the defective pixels. Note that such correction devices may be incorporated in the imaging control unit 13 or the console unit 14 to carry out correction of the various functions in the imaging control unit 13 or the console unit 14.

Figure 7:
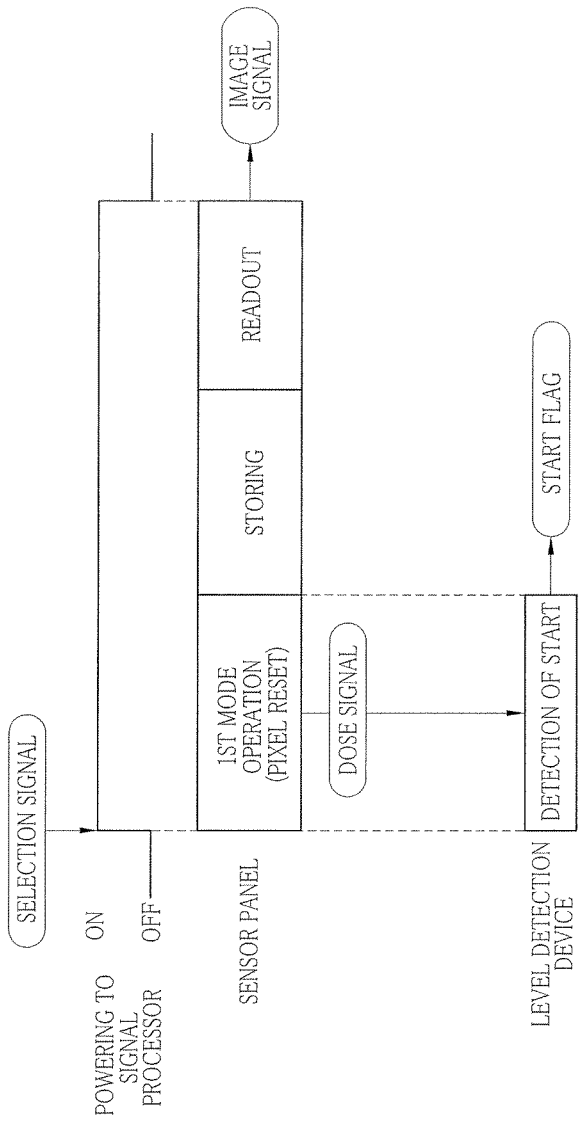
FIG. 7 is a timing chart illustrating supply of power to the selected electronic cassette.
Figure 8:
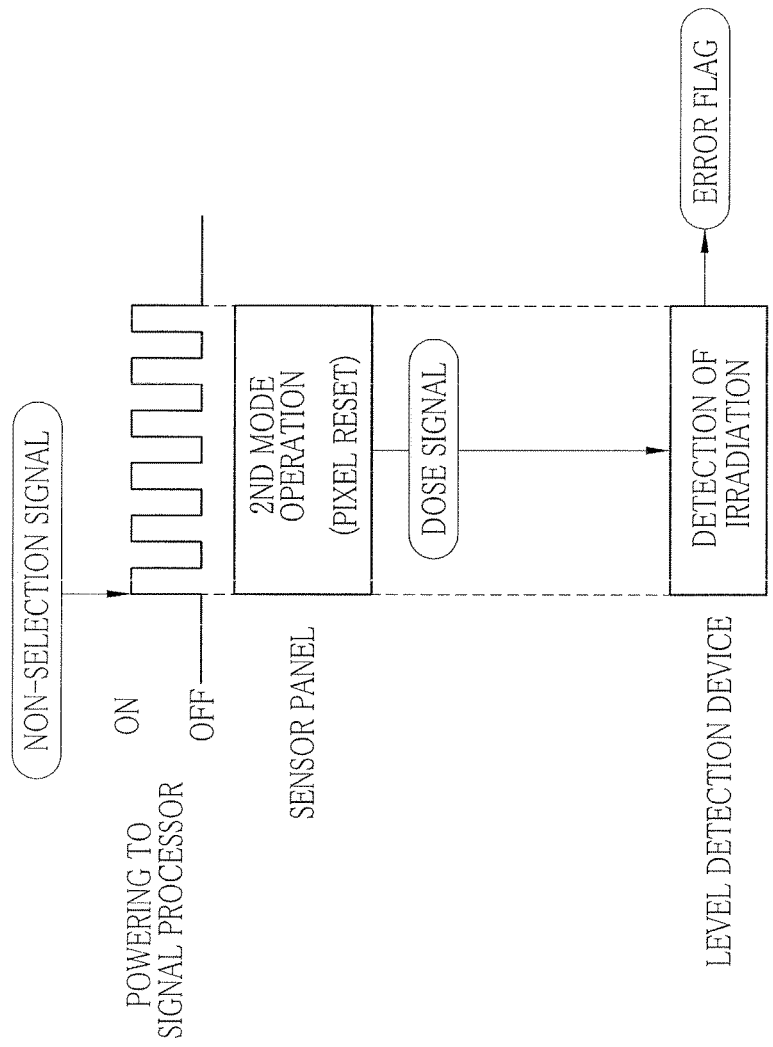
FIG. 8 is a timing chart illustrating supply of power to the unselected electronic cassette.

In FIGS. 7 and 8, the controller 54 before irradiation of X-rays sets the electronic cassette 12 in a standby state in which only the communication interface 33 operates without powering the gate driver 50 and the signal processor 51. In case a selection signal or non-selection signal is received from the console unit 14 through the communication interface 33, the controller 54 starts supplying the gate driver 50 and the signal processor 51 with power. Upon receiving the selection signal, the controller 54 causes the sensor panel 30 to start a first mode operation (normal). Upon receiving the non-selection signal, the controller 54 causes the sensor panel 30 to start a second mode operation (auxiliary). The first and second mode operations in the sensor panel 30 are the pixel reset. FIG. 7 illustrates the condition of the selected cassette. FIG. 8 illustrates the condition of the unselected cassette.

In FIG. 7, the level detection device 53 of the selected cassette, upon detecting a start of irradiation of the X-ray imaging apparatus 10, outputs a start flag (start detection signal) to the controller 54. In response to the start flag, the controller 54 controls the sensor panel 30 and sets the same from the pixel reset to the storing. Even while the pixel reset is performed incompletely at one of the pixel rows disposed intermediately, the controller 54 interrupts the pixel reset and starts the storing in the sensor panel 30.

In the storing, the gate driver 50 does not provide any of the scan lines 41 with the gate pulse G(K). The thin film transistors 45 are turned off during the storing. The pixels 40 store signal charge according to an incident radiation dose of X-rays. In case the elapsed time in the timer 60 becomes equal to the irradiation time determined in the imaging condition, the controller 54 terminates the storing and starts reading out an image.

Figure 9:
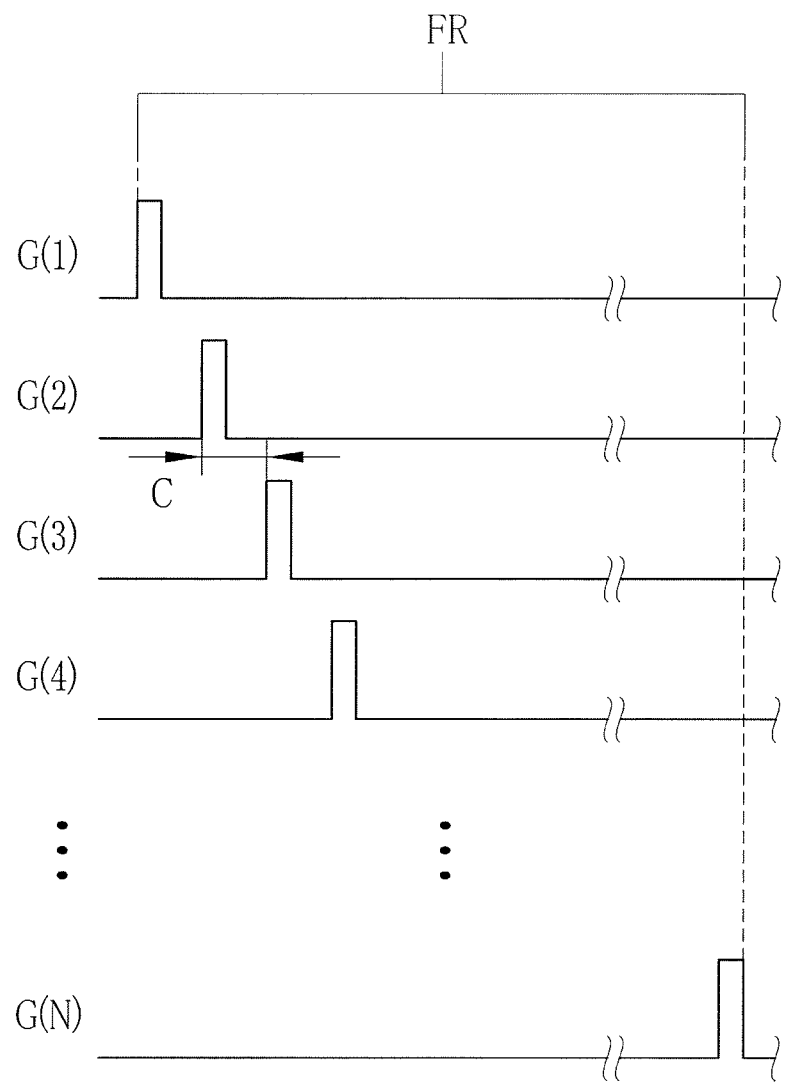
FIG. 9 is a timing chart illustrating a state of generating a gate pulse in image readout.

In the image readout in FIG. 9, the gate driver 50 supplies the gate pulse G(K) to the scan lines 41 sequentially at a predetermined interval C from the first pixel row to the Nth pixel row, to turn on the thin film transistors 45 by one pixel row in connection with the scan lines 41. A length of time while the thin film transistors 45 are turned on is determined by a pulse width of the gate pulse G(K). Upon lapse of the time according to the pulse width, the thin film transistors 45 become turned off again. Note that a sign FR denotes the pixel reset of one frame from the first pixel row to the Nth pixel row.

After the image reading, the controller 54 terminates power supply to the gate driver 50 and the signal processor 51, and sets again the selected cassette in the standby state. See FIG. 7.

In FIG. 8, the level detection device 53 of the unselected cassette, upon detecting the irradiation of X-rays, outputs an error flag (erroneous selection signal) to the controller 54 to inform an error in the selection of the electronic cassette 12 at the console unit 14. The controller 54 interrupts powering to the gate driver 50 and the signal processor 51 in response to the error flag from the level detection device 53, to set the unselected cassette in the standby state again. Assuming that the pixel reset is performed incompletely at one of the pixel rows disposed intermediately, the pixel reset is performed up to the Nth pixel row. The pixel reset FR of one frame is completed before setting to the standby state. Also, the controller 54 transmits the error flag from the communication interface 33 to the console unit 14.

Figure 10:
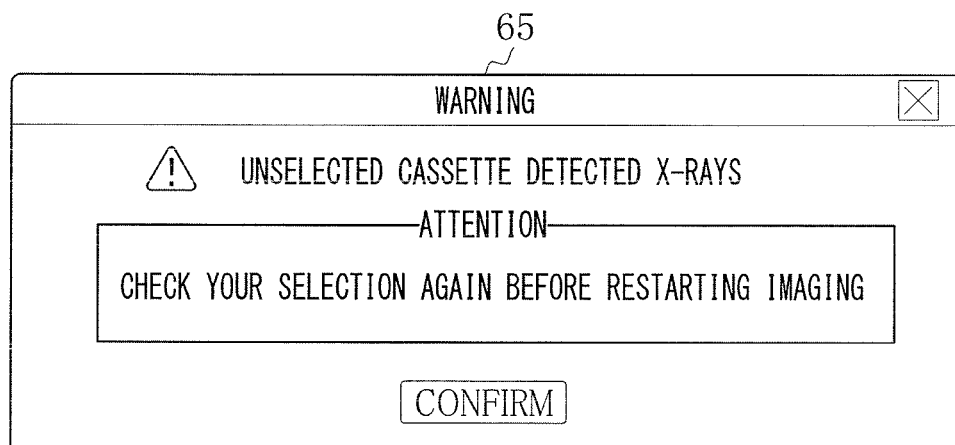
FIG. 10 is a front elevation illustrating an alarm screen on a display panel.

In case the error flag is received, an alarm screen 65 is displayed on the display panel 14b by the console unit 14 in a popup form as illustrated in FIG. 10. The alarm screen 65 displays a warning message and an instruction message. An example of the warning message is "UNSELECTED CASSETTE DETECTED X-RAYS" to inform an error in the selection of the electronic cassette 12 with the console unit 14. An example of the instruction message is "CHECK YOUR SELECTION AGAIN BEFORE RESTARTING IMAGING" for encouraging check and next imaging of the electronic cassette 12. The console unit 14 constitutes a display device. Furthermore, it is possible to generate sound as information of an alarm message in place of or in addition to the alarm screen 65, for example, beep sound. Examples of sound sources of the sound are a loudspeaker, buzzer and the like.

In the pixel reset, operation of the gate driver 50 is the same as image readout in FIG. 9. In the pixel reset, charge is swept from a first pixel row to an Nth pixel row by one pixel row. Upon completing sweep of the charge of one frame after sweeping of the Nth pixel row, then sweeping is repeated by return to the first pixel row. This is a sequential reset of a method of pixel reset. See FIGS. 12 and 13.

In the image readout operation, the controller 54 drives elements in the gate driver 50 and the signal processor 51 at a predetermined period, the elements including the integrating amplifiers 55, the correlated double samplers 57, the multiplexer 58 and the A/D converter 59. The controller 54 sequentially selects the scan lines 41 from the first pixel row to the Nth pixel row, and writes the signal voltage to the memory 52 sequentially, the signal voltage being for one pixel row output by the A/D converter 59. Upon termination of the image readout of one frame from the first pixel row to the Nth pixel row, the memory 52 stores the signal voltage of one frame of an X-ray image in association with the X and Y coordinates of the pixels 40. Data of the signal voltage is readout from the memory 52 by the controller 54, which processes the data for correction of various functions, before the data is transmitted by the communication interface 33 to the console unit 14. Finally, the X-ray image of the body H is detected. Note that the signal voltage read out in the image readout is referred to as an image signal herein. See FIG. 7.

In pixel reset, signal charge flows from the pixels 40 through the signal lines 42 to the capacitors 55b of the integrating amplifiers 55 while the thin film transistors 45 are turned on. In a manner similar to the image readout, the signal processor 51 reads out a signal voltage. The memory 52 stores the signal voltage of one pixel row each time of completing the pixel reset of one pixel row. The signal voltage of one pixel row stored in the memory 52 is output to the level detection device 53, which refers to the signal voltage to detect a start of irradiating X-rays and detect the irradiation. Note that the signal voltage read out by the pixel reset is hereinafter referred to as a dose signal. See FIGS. 7 and 8.

Before applying X-rays, charge flowing from the pixels 40 to the capacitors 55b is dark current charge. A dose signal is approximately zero. In case irradiation of X-rays is started, charge flowing from the pixels 40 to the capacitors 55b changes according to an incident radiation dose of X-rays upon the active pixel area 43. A dose signal at this time is information of dose of X-rays upon reaching the active pixel area 43 per unit time, at an interval C of the pixel reset for one pixel row.

In the pixel reset, the amplifier reset switch 55c of the integrating amplifiers 55 is supplied with an amplifier reset pulse by the controller 54 to reset the stored charge at each time of the pixel reset of one pixel row, which is similar to the image readout. In the pixel reset of one pixel row, the correlated double samplers 57 are sequentially selected by the multiplexer 58, to output a dose signal of one pixel row to the memory 52. The memory 52 stores the dose signal of the one pixel row in correspondence with X and Y-coordinates of the pixels 40.

Figure 11A:
FIGS. 11A and 11B are timing charts illustrating first and second mode operations.
Figure 11B:
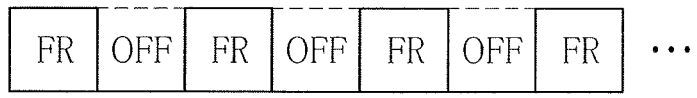

In FIG. 12, the structure of FIGS. 11A and 11B is illustrated specifically. For the selected cassette, the controller 54 causes the sensor panel 30 to perform the pixel reset FR for one frame continuously as first mode operation. During the pixel reset, the gate driver 50 and the signal processor 51 are supplied with power and driven by the battery 32 continuously. See FIG. 7.

Figure 13:
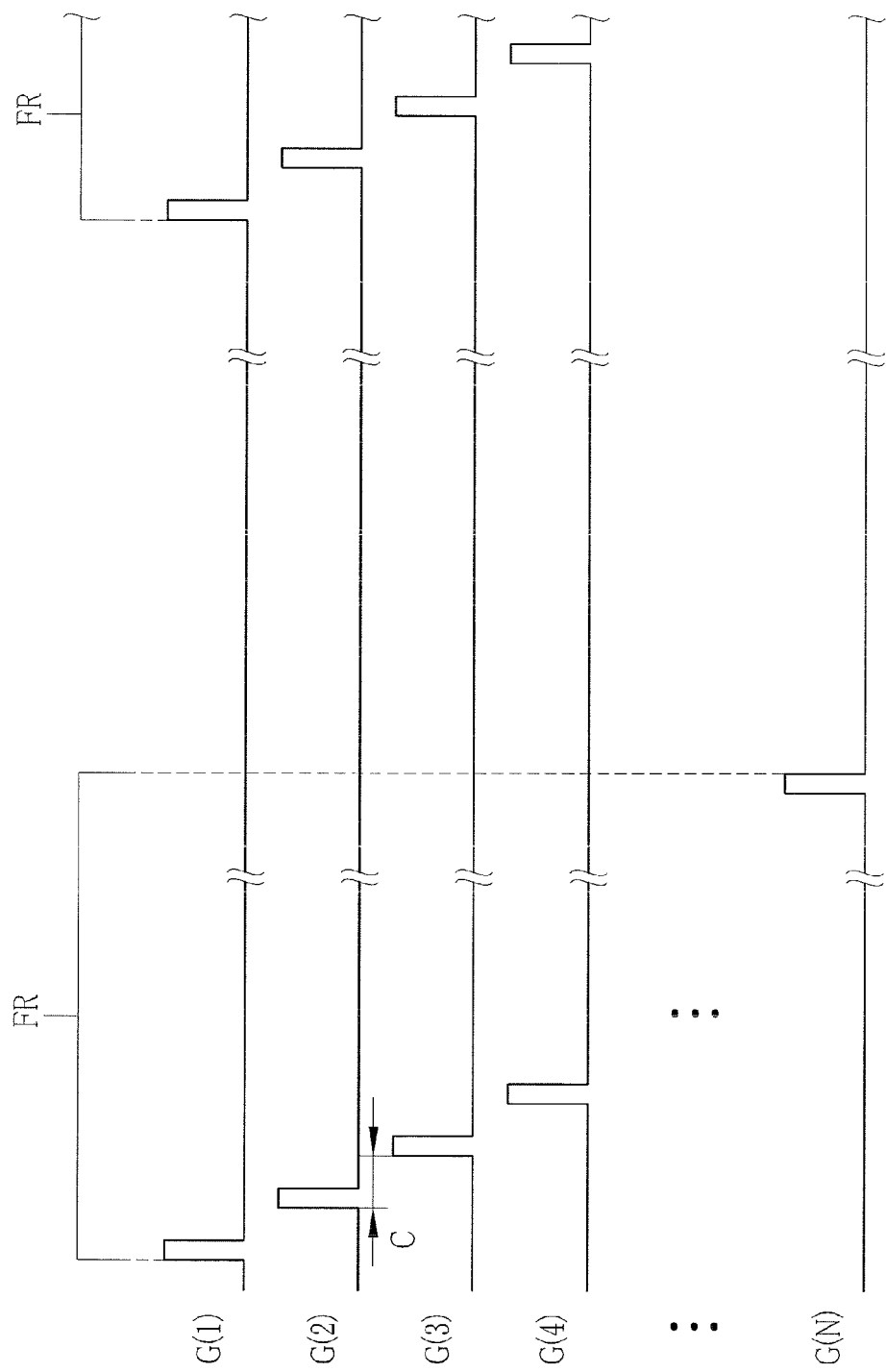
FIG. 13 is a timing chart illustrating a state of generating a gate pulse in the second mode operation.

As illustrated in FIGS. 11B and 13, the controller 54 causes the sensor panel 30 to carry out the second mode operation of pixel reset FR of one frame at a longer interval than the first mode operation in relation to the unselected cassette. In the first mode operation, the pixel reset FR of a second frame is started immediately after the pixel reset FR of a first frame. In contrast with this, in the second mode operation, one period for the pixel reset FR of one frame is set as idle time between preceding and succeeding frames.

While the pixel reset FR of one frame is interrupted, the gate driver 50 and the signal processor 51 are not supplied with power by the battery 32 in the same manner as the standby state, and are not driven. See FIG. 8. Thus, driving power is lower in the second mode operation than in the first mode operation. In the present embodiment, the pixel reset FR of one frame is interrupted for one time. Driving power is one half as high in the second mode operation as in the first mode operation.

Assuming that the level detection device 53 does not detect a start of irradiation of X-rays even upon lapse of predetermined time, or does not detect the irradiation of X-rays even upon lapse of the predetermined time, then the controller 54 terminates the first or second mode operation, to set the electronic cassette 12 in the standby state again.

Figure 14:
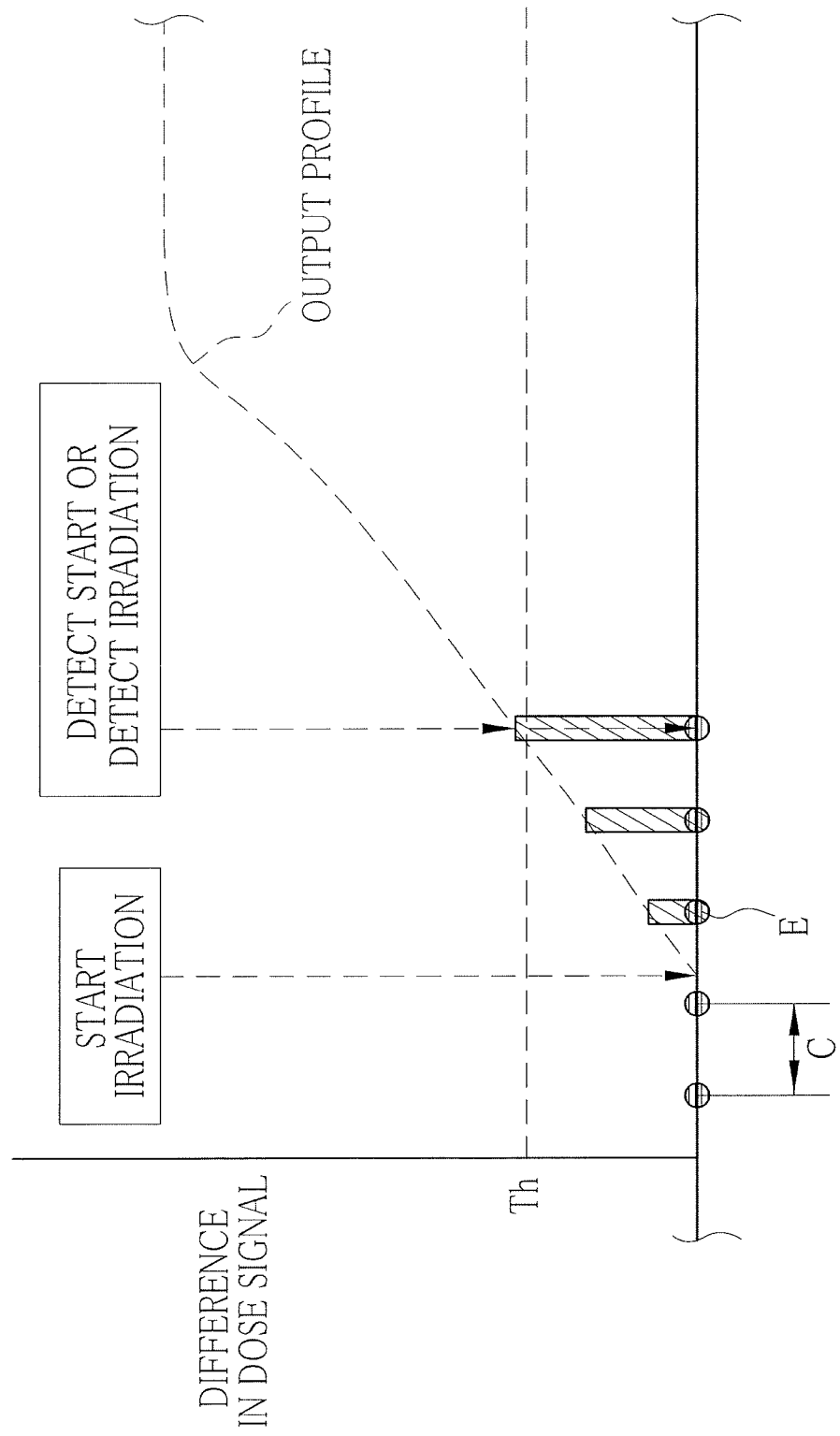
FIG. 14 is a graph illustrating an output profile of irradiation and a difference in a dose signal.

In FIG. 14, an output profile of irradiation (indicated by the broken line) is illustrated for a change of dose of X-rays from the X-ray source 15 per unit time. The dose per unit time is low shortly after the start of the irradiation, but gradually increases toward a target dose according to the tube current. Note that a dot with the reference sign E indicates a time point of the output of the dose signal of one pixel row. Before irradiation of X-rays, the dose signal is an output according to the dark current charge, and as small as zero or a very low value in comparison with an output according to the dose of X-rays. After starting irradiation of X-rays, the dose signal increases according to the output profile of the irradiation of X-rays.

The level detection device 53 includes an internal memory for storing a dose signal of one pixel row sequentially output at an interval C for a stock of one time. The level detection device 53 acquires a difference between a previous dose signal read from the internal memory and a present dose signal read newly from the memory 52, and compares the difference with a predetermined detection threshold Th. For the purpose of detecting the start and irradiation rapidly and correctly, it is preferable to use a relatively large value of a dose signal, because of small influence upon attenuation depending upon an object. A preferable example of value of a dose signal for the comparison with the detection threshold Th is the maximum of a dose signal of one pixel row, and also can be an average or total of the dose signal of one pixel row. The dose signal increases upon starting the irradiation of X-rays, so that the difference between the previous and present dose signals becomes higher than the detection threshold Th. In response to the increase of the difference over the detection threshold Th, the level detection device 53 detects the start of the irradiation from the X-ray source 15 or detects the irradiation. Note that the start or irradiation can be detected by comparison of the present dose signal with the detection threshold Th, in place of using the difference between the previous and present dose signals.

Figure 15:
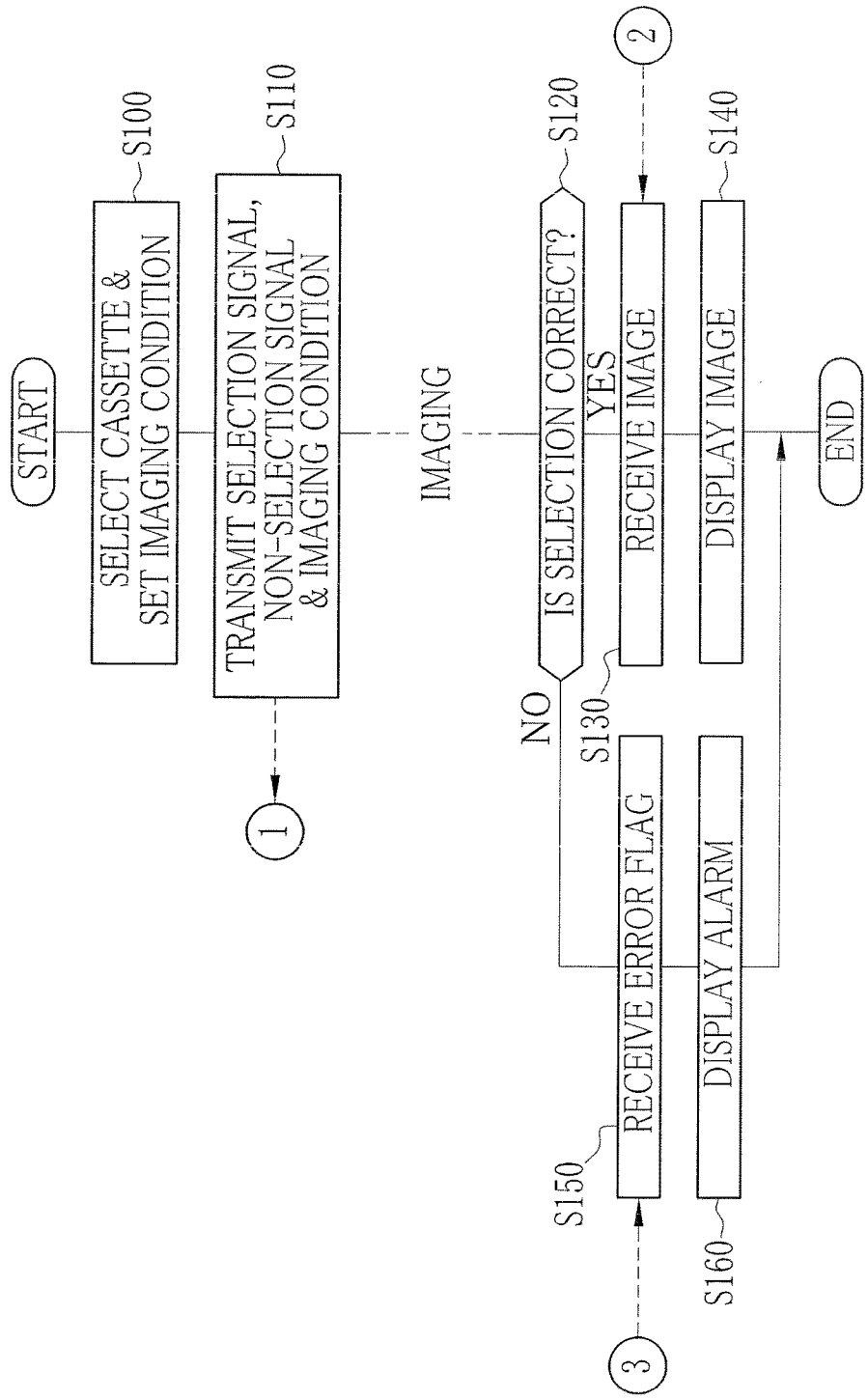
FIG. 15 is a flow chart illustrating operation of a console unit.
Figure 16:
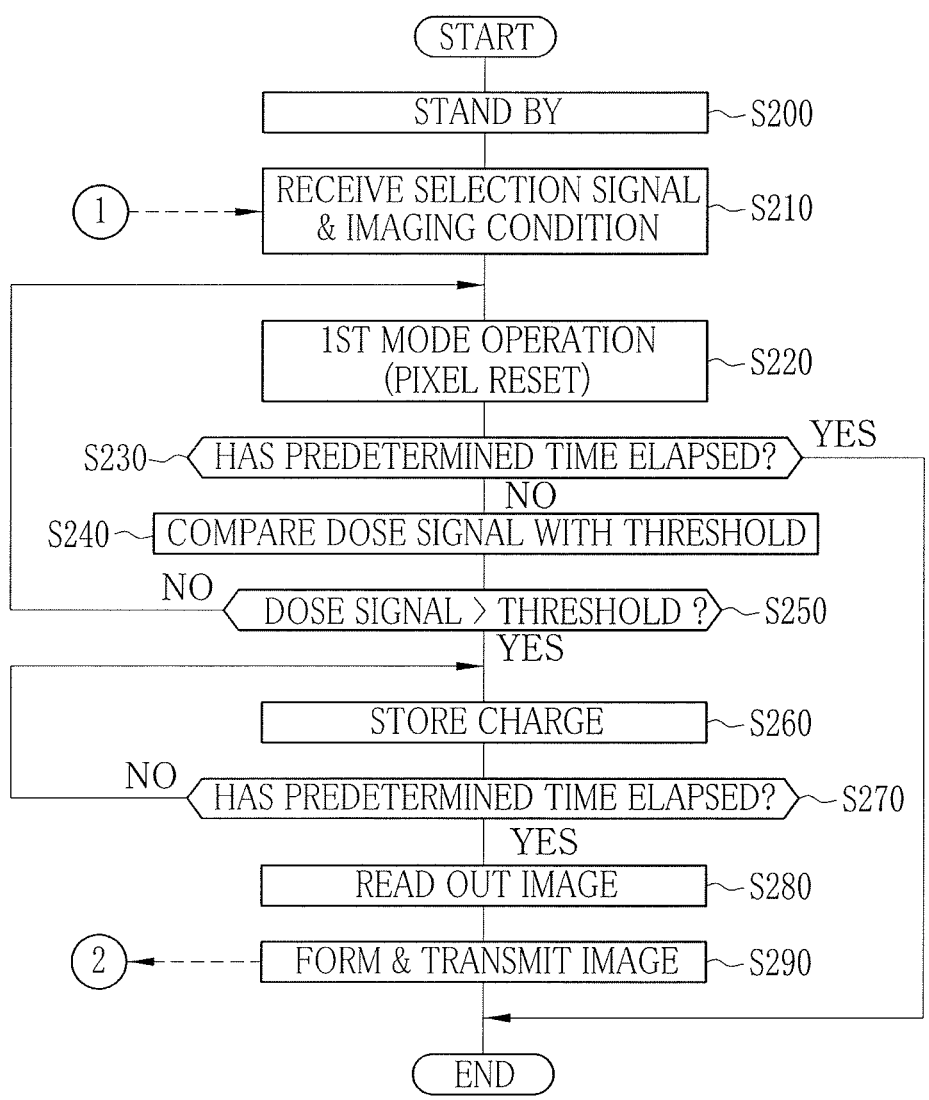
FIG. 16 is a flow chart illustrating operation of a selected electronic cassette.
Figure 17:
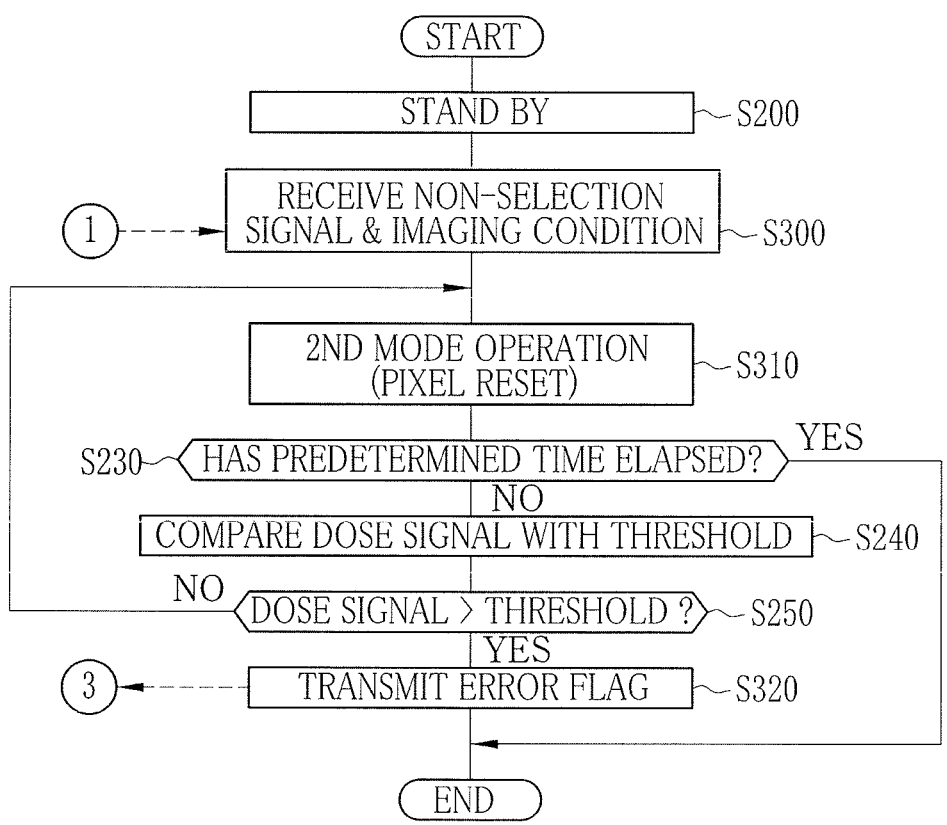
FIG. 17 is a flow chart illustrating operation of an unselected electronic cassette.

The operation of the above construction is described now by referring to FIGS. 15, 16 and 17. FIG. 15 illustrates operation of the console unit 14. FIG. 16 illustrates operation of the selected cassette. FIG. 17 illustrates operation of the unselected cassette.

For X-ray imaging in the X-ray imaging system 2, at first the body H is set on the floor stand 17 or the imaging table 18 for the erect or supine posture. A height or horizontal position of the electronic cassette 12 is adjusted for suitably positioning a body part or object of interest in the body H. A height, horizontal position, and size of radiation field are adjusted according to the position of the electronic cassette 12 and the size of the object of interest.

As indicated at the step S100 in FIG. 15, the console unit 14 selects the electronic cassette 12 for use among the electronic cassettes 12a and 12b, and also inputs an imaging condition. The same irradiation condition of the X-rays as the console unit 14 is set in the source driver 16. Information of the imaging condition from the console unit 14 is transmitted to the imaging control unit 13 with the selection signal or non-selection signal, and then transferred from the imaging control unit 13 to the electronic cassette 12 in the step S110. The selection signal is sent to the selected cassette. The non-selection signal is sent to the unselected cassette.

After the imaging condition is set in the console unit 14 and the irradiation condition is set in the source driver 16, then the physician or operator depresses the start switch 20 halfway. In response, a warmup signal is input to the source driver 16 to start warming up the X-ray source 15.

In FIG. 16, the selected cassette waits for a selection signal from the console unit 14 and the imaging condition in the standby in the step S200. The selected cassette, upon receiving the selection signal from the console unit 14 with the imaging condition in the step S210, starts the first mode operation in the step S220. In the first mode operation, the pixel reset FR of one frame is performed continuously. It is possible to detect a time point of starting irradiation of X-rays unfailingly owing to the continuous operation of the pixel reset FR of one frame.

In the pixel reset, the dark current charge stored in the pixels 40 is swept to the signal lines 42, to reset the pixels 40. A dose signal according to the signal charge stored in the integrating amplifiers 55 is read one pixel row after another through the signal lines 42. The signal charge stored in the integrating amplifiers 55 is reset at each time of pixel reset of one pixel row. To this end, the correlated double samplers 57 are sequentially selected by the multiplexer 58, to write the dose signal of one pixel row to the memory 52. At each time of this storing, the level detection device 53 reads the dose signal of one pixel row from the memory 52, acquires a difference between maximum values of previous and present dose signals of one pixel row, and then compares the difference with the detection threshold Th. See the step S240.

Before starting application of X-rays, the dose signal only includes an output corresponding to the dark current charge. The dose signal is approximately zero. A difference in the dose signal is equal to or less than the detection threshold Th. In case the electronic cassette 12 is depressed fully by an operator, the X-ray imaging apparatus 10 emits X-rays. A dose of X-rays per unit time is low immediately after starting the X-ray imaging apparatus 10, but is gradually increased. A value of the dose signal is low immediately after starting the X-ray imaging apparatus 10. Upon an increase in the dose of X-rays, signal charge increases at the pixels 40. In case the pixel reset is performed, the stored signal charge is swept to the signal lines 42. Therefore, the value of the dose signal obtained by the pixel reset of one pixel row is increased. After this, the difference in the dose signal becomes more than the detection threshold Th. The level detection device 53 detects the start of irradiating X-rays (yes in the step S250), and outputs a start flag to the controller 54. As a result, the electronic cassette 12 selected for use in the console unit 14 is found to coincide with the electronic cassette 12 to which X-rays are applied upon detecting the start of irradiation of X-rays in the level detection device 53. Namely, it is found that the selection of the electronic cassette 12 has been correct with the console unit 14 (yes in the step S120 in FIG. 15).

Assuming that no start of irradiation is detected by the level detection device 53 even at a lapse of the predetermined time (yes in the step S230), then the first mode operation of the selected cassette is terminated to return to the standby state. There are plural possibilities of this situation. For example, the imaging may be interrupted for an incidental reason. Otherwise, the electronic cassette 12 selected for use at the console unit 14 is found to be different from the electronic cassette 12 to which X-rays are applied. Namely, an error is found in the selection of the electronic cassette 12 at the console unit 14 (no in the step S120 in FIG. 15).

In response to the start flag from the level detection device 53, the controller 54 turns off all the thin film transistors 45 to terminate the pixel reset, and start the sensor panel 30 for the storing in the step S260. In the storing, the gate driver 50 does not generate a gate pulse. The pixels 40 store signal charge according to a dose of emitted X-rays. Thus, the start of irradiating X-rays is synchronized with the start of storing. At the same time, the timer 60 of the controller 54 starts measuring time.

In case the measured time in the timer 21 becomes equal to the predetermined irradiation time, the X-ray source apparatus 11 terminates irradiation of X-rays from the X-ray imaging apparatus 10. In case the measured time in the timer 60 becomes equal to the predetermined irradiation time according to the imaging condition (yes in the step S270), the controller 54 controls the sensor panel 30 and sets this from the storing to the image readout. See the step S280. In the image readout, the gate driver 50 generates a gate pulse to read out the signal charge of the pixels 40 of one pixel row to the signal lines 42. An image signal of one pixel row according to the signal charge is output from the integrating amplifiers 55, converted digitally, and stored to the memory 52. Those steps are repeatedly carried out in the image readout. Thus, the image signal of the X-ray image of one frame is written to the memory 52. The controller 54 corrects the X-ray image for various correcting functions, before the communication interface 33 transmits the X-ray image to the imaging control unit 13. See the step S290.

In the step S130 of FIG. 15, the X-ray image is transferred by the imaging control unit 13 to the console unit 14. The console unit 14 upon reception causes the display panel 14b to display the X-ray image for diagnosis in the step S140.

In FIG. 17, the unselected cassette, upon receiving a non-selection signal from the console unit 14 with the imaging condition (step S300), starts the second mode operation (step S310). The pixel reset FR of one frame is performed at a longer interval in the second mode operation than in the first mode operation. During idle time of the pixel reset FR of one frame, no power is supplied to the gate driver 50 and the signal processor 51 by the battery 32. Thus, driving power in the second mode operation is lower than in the first mode operation. Wasteful use of power in the battery 32 for the unselected cassette can be prevented. The problem of early power consumption of the battery can be prevented. It is unnecessary frequently to recharge the battery for the purpose of imaging.

In the second mode operation, a dose signal of one pixel row is recorded to the memory 52 upon the pixel reset of each one pixel row, and read out by the level detection device 53. The level detection device 53 of the unselected cassette compares a difference in the dose signal with the detection threshold Th in the step S240 in a manner similar to the selected cassette, and assuming that the difference is larger than the detection threshold Th, detects irradiation of X-rays (yes in the step S250). The level detection device 53 outputs an error flag to the controller 54 in the step S320. Should the level detection device 53 in the unselected cassette detect application of X-rays, it is found that selection of the electronic cassette 12 at the console unit 14 is wrong (no in the step S120 in FIG. 15).

Assuming that no irradiation of X-rays is detected by the level detection device 53 even upon lapse of the predetermined time (yes in the step S230), the unselected cassette terminates the second mode operation to return to the standby state, in a manner similar to the selected cassette. The imaging may be interrupted for an incidental reason. Otherwise, correctness is found in the selection of the electronic cassette 12 at the console unit 14 (yes in the step S120 in FIG. 15).

In case an error flag is received from the unselected cassette in the step S150 of FIG. 15, the console unit 14 causes the display panel 14b to display the alarm screen 65 in the step S160. The operator can recognize the error in selecting the electronic cassette 12 by viewing the alarm screen 65. He or she selects the electronic cassette 12 again with the selection screen 26, or repositions the electronic cassette 12 selected initially for receiving X-rays, so that the electronic cassette 12 being selected is caused to coincide with the electronic cassette 12 receiving X-rays. Then an image is formed again.

In the first embodiment, the electronic cassettes 12 are two. However, the number of the electronic cassettes 12 can be more than two. The interval of the pixel reset FR of one frame in the second mode operation is not limited to a period of one time of the pixel reset FR of one frame in the first embodiment, but can be changed suitably. However, it is necessary to output a dose signal for at least one time during the irradiation time determined by the irradiation condition for the purpose of reliably detecting the irradiation of X-rays. Thus, a preferable interval of the pixel reset FR of one frame in the second mode operation is equal to or less than the irradiation time. It is possible automatically to change the interval of the pixel reset FR of one frame in the second mode operation according to the irradiation time.

In the first embodiment, a function of the user input interface for selecting the electronic cassette 12 for use is provided in the console unit 14. However, the imaging control unit 13 can have a function of a user input interface. Also, a selection switch can be provided in the electronic cassette 12 for active and inactive states, so that the electronic cassette 12 can have a function of a user input interface. Furthermore, an external device can be used for inputting selection of the electronic cassette 12 externally as user input interface.

In the first embodiment, the console unit 14 has the function of the display device for displaying information of an error in the selection of the electronic cassette 12. However, a function of the display device can be provided on the imaging control unit 13 or the electronic cassette 12 in a manner similar to a user input interface. Also, a specialized display device can be used, such as an alarm lamp or the like.

In the above embodiment, the user input interface 14a is separate from the display panel 14b in the console unit 14. However, the user input interface 14a and the display panel 14b can be constituted together as components of a single apparatus. In the above embodiment, the console unit 14 is a stationary type without portability. However, the console unit 14 can be a portable terminal apparatus, such as a laptop computer and a tablet. The tablet includes a touchscreen device or touchscreen panel, in which the user input interface 14a and the display panel 14b can be included together.

Various types of electric noise occur in circuit elements such as the signal processor 51, including periodic noise created incessantly, and vibration noise created by external shock or vibration. As the dose signal may contain such noise, the level of the dose signal will be higher than the detection threshold Th in monitoring the start and the irradiation irrespective of turn-off of X-rays. It is likely erroneously to detect the start and the irradiation of X-rays. In view of this, it is preferable to prevent those errors in the level detection.

To prevent erroneous detection, it is possible to carry out the start detection and the irradiation detection in first and second steps of detection. In the first step, it is judged whether the level of the dose signal becomes higher than the detection threshold Th. Assuming that it is found in the first step that the level of the dose signal becomes higher than the detection threshold Th, then the second step is carried out to check correctness of the first step. In the second step, a change in the dose signal with time is monitored. Assuming that the level of the dose signal continues higher than the detection threshold Th for a predetermined period, then correctness of the first step is found.

Second Preferred Embodiment

It is technically known that charge partially remains in the pixels 40 even after reading out an image signal in the readout operation. Residual charge causes image lag, in which an X-ray image of next imaging is influenced to lower its image quality. In view of this, there is a known method of correcting image lag for an X-ray image.

Figure 18:
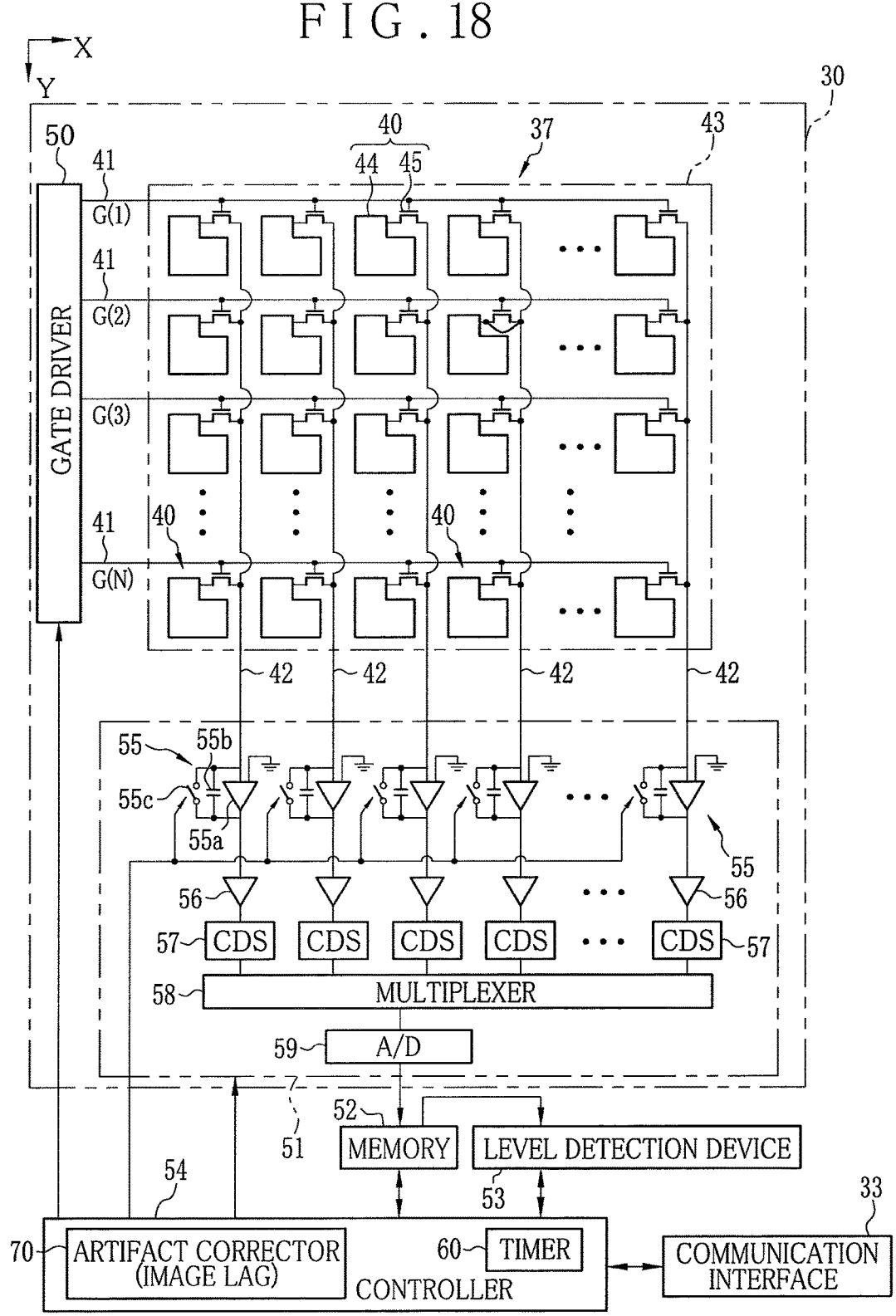
FIG. 18 is a block diagram schematically illustrating a second preferred embodiment having an artifact corrector for image lag.

In FIG. 18, an artifact corrector 70 (image lag) is incorporated in the controller 54. The electronic cassette 12 operates for correcting image lag. Elements similar to those of the above embodiment are designated with identical reference numerals.

Figure 19:
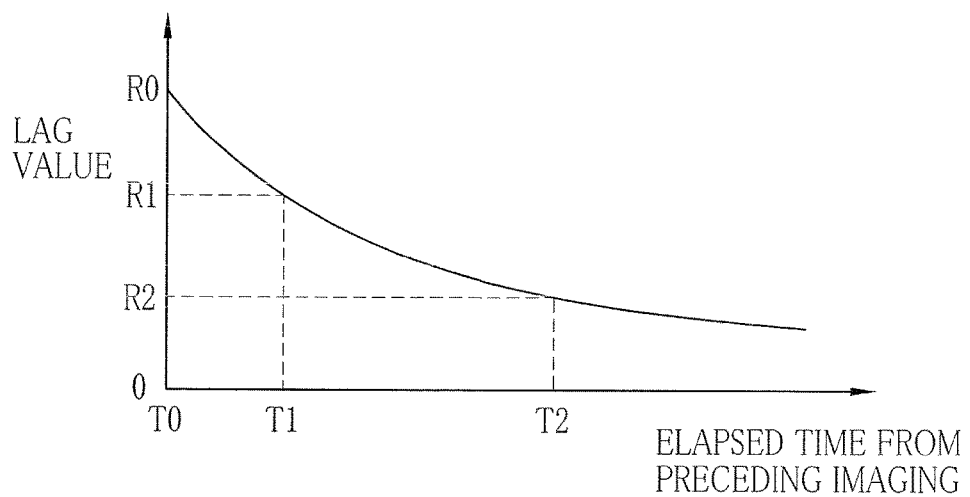
FIG. 19 is a graph illustrating a relationship between a lag value and elapsed time.

The artifact corrector 70 processes the X-ray image in the artifact correction of image lag according to lag value information of a relationship between a lag value of charge remaining at the pixels 40 in the preceding imaging and elapsed time from the preceding imaging. See FIG. 19. The lag value information is obtained by previously measuring changes in the lag value with time under various irradiation conditions according to experiments or simulation. The lag value information is stored in an internal memory (not shown) in the controller 54 in a form of a look-up table or function according to a result of the experiments or simulation. The artifact corrector 70 reads out the lag value information from the internal memory according to the irradiation condition, to perform the artifact correction of image lag.

Figure 20:
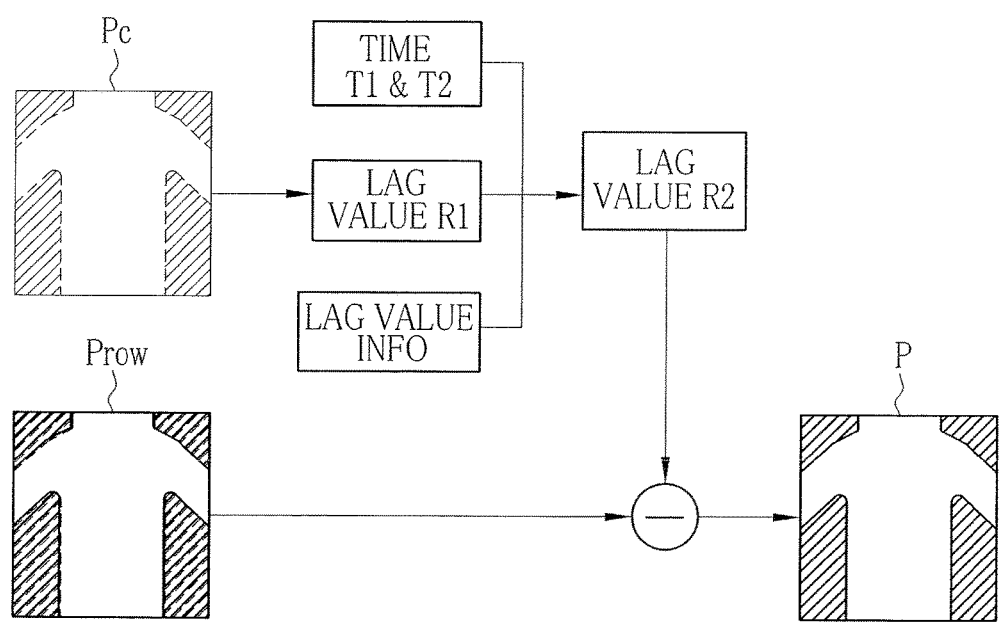
FIG. 20 is a flow diagram illustrating operation of the artifact correction of image lag.

The lag value decreases with time from the lag value R0 immediately after the preceding imaging at the time T0 (immediately after the image readout). In FIG. 20, the controller 54 receives information of the imaging condition and a selection signal or non-selection signal from the console unit 14 after the preceding imaging and before next imaging (time T1). Then the controller 54 causes the sensor panel 30 to operate for the image readout, to output an X-ray image Pc for artifact correction of image lag. The X-ray image Pc for the artifact correction of image lag is output to the internal memory in the controller 54 from the memory 52, and stored in the internal memory. The artifact corrector 70 obtains a lag value R1 at the time T1 according to the X-ray image Pc for the artifact correction of image lag. Then the lag value R2 at the time T2 of next imaging is estimated according to the determined lag value R1, lag value information, time T1 and time T2 of next imaging. The estimated lag value R2 is subtracted from the image signals of an X-ray image Prow of next imaging, to acquire an X-ray image P after removing influence of lag from the X-ray image Prow. The times T1 and T2 are measured by the timer 60. Time information is obtained, and supplied to the artifact corrector 70. Assuming that the estimated lag value R2 is equal to or less than a predetermined threshold, it is possible not to correct the lag, because no influence occurs to image quality of the X-ray image.

In the first embodiment, assuming that the selection of the electronic cassette 12 is erroneous, a physician or operator selects the electronic cassette 12 again with the selection screen 26, or repositions the electronic cassette 12 selected initially for receiving X-rays. In view of saving manual operation for setting, it is more likely that he or she selects the electronic cassette 12 again with the selection screen 26 for creating a new image. However, there is risk in that the unselected cassette is selected as the selected cassette by use of the selection screen 26 before complete disappearance of image lag of the unselected cassette with erroneously applied X-rays, so that an image is created considerably shortly.

Figure 21:
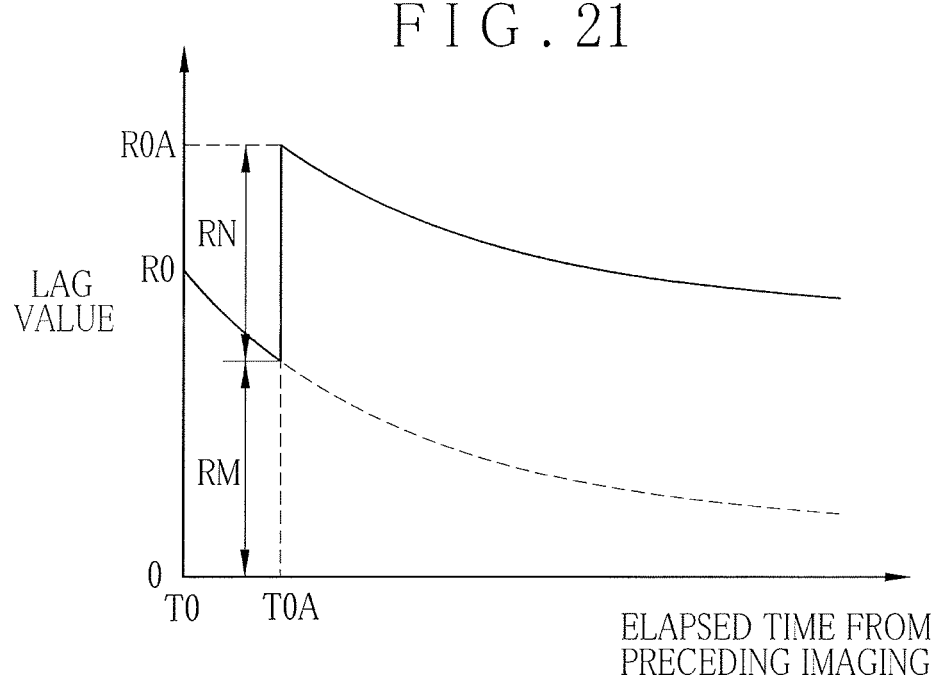
FIG. 21 is a graph illustrating a relationship between the lag value and elapsed time in a state after an error in the selection.

In FIG. 21, the lag value R0A of next imaging (time T0A) is constituted by combined components of a lag value RM at the time T0A with X-rays erroneously applied at the time T0, and a lag value RN with X-rays applied for next imaging at the time T0A. The manner of decrease in the lag value is different from the lag value information in a normal state without erroneous selection of the broken line. Assuming that correction is carried out according to the lag value information in the normal state, a deviation may occur in the estimation of the lag value. It is impossible to perform the correction correctly.

Figure 22:
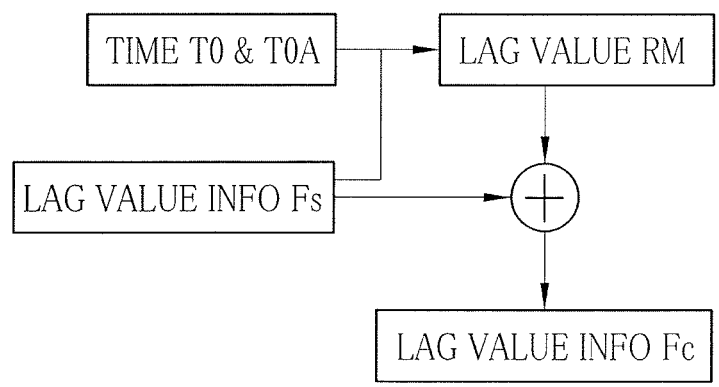
FIG. 22 is a flow diagram illustrating a change in the lag value.

In FIG. 22, the operation of the artifact corrector 70 at the time of erroneous selection of the electronic cassette 12 is illustrated. The artifact corrector 70 acquires time information of time T0 and T0A, and determines the lag value RM due to erroneously applied X-rays according to the time information and the lag value information Fs at the normal time. The lag value RM is cumulatively added to a lag value of the lag value information at the normal time, to update the lag value information Fs to the lag value information Fc. Then next lag value R2 of next imaging is estimated according to the updated lag value information Fc. Accordingly, correct processing of lag images can be carried out even after selecting the electronic cassette 12 again for next imaging due to the previous erroneous selection, so that an X-ray image of good image quality can be formed.

Furthermore, it is possible to provide a function for correction of image lag in the imaging control unit 13 or the console unit 14 in place of the electronic cassette 12. Also, a separate device for correction of image lag can be used in combination.

Various modifications of the second mode operation can be constructed with differences from the first embodiment in which an interval of the pixel reset FR for one frame is set long. See third, fourth and fifth embodiments below.

Third Preferred Embodiment

Figure 23:
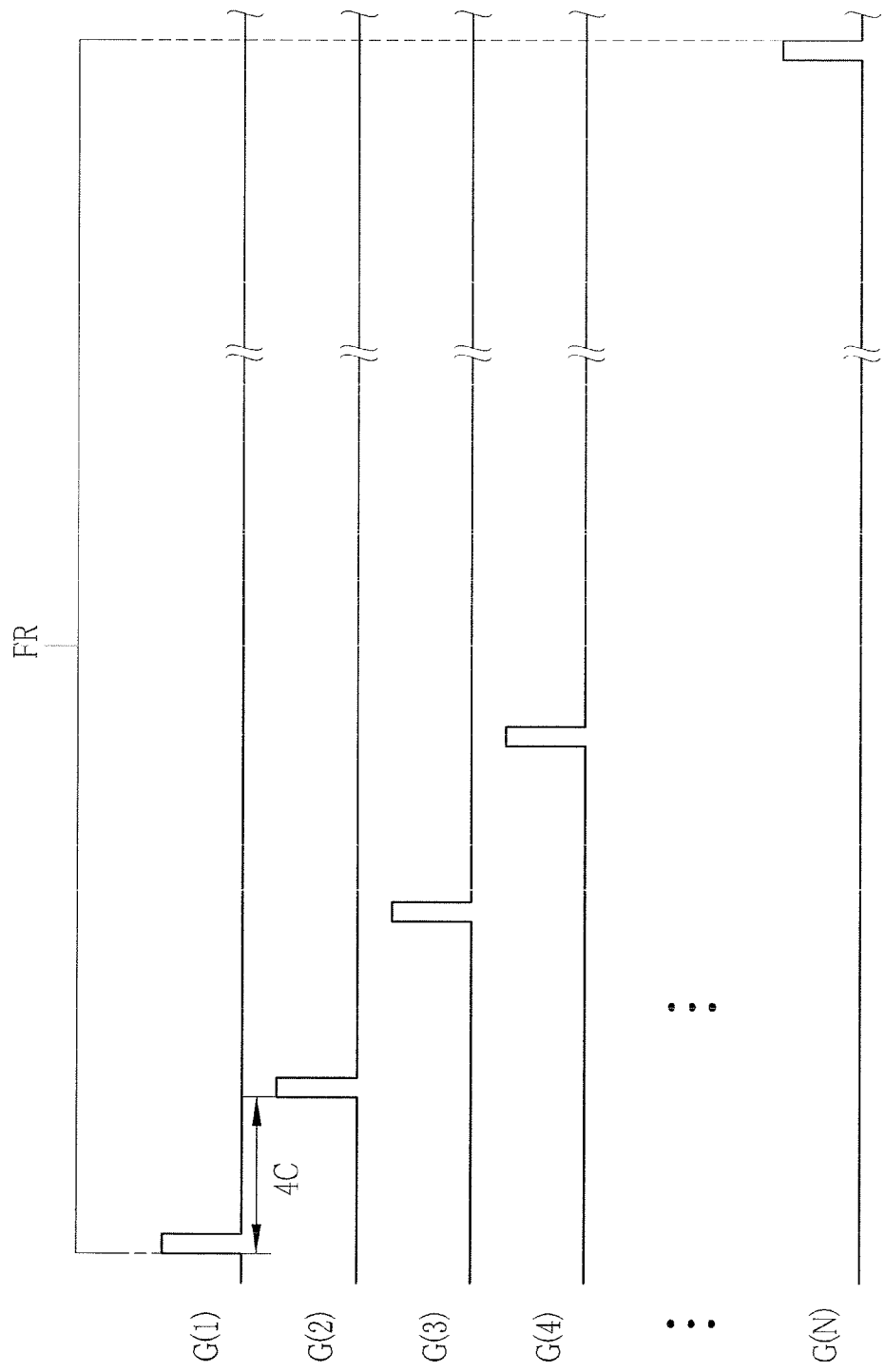
FIG. 23 is a timing chart illustrating a state of generating a gate pulse in the second mode operation in a third preferred embodiment.

In the second mode operation, the controller 54 causes the sensor panel 30 to perform the pixel reset of one pixel row at a longer interval than in the first mode operation. In FIG. 23, let C be the interval of the pixel reset of one pixel row of the first mode operation in a manner similar to the first embodiment. An interval of the pixel reset of one pixel row of the second mode operation is 4C which is four times as high as C. Accordingly, the number of events of driving the gate driver 50 and the signal processor 51 per unit time is smaller in the second mode operation than in the first mode operation. Driving power for the second mode operation can be set lower than the first mode operation.

Fourth Preferred Embodiment

Figure 24:
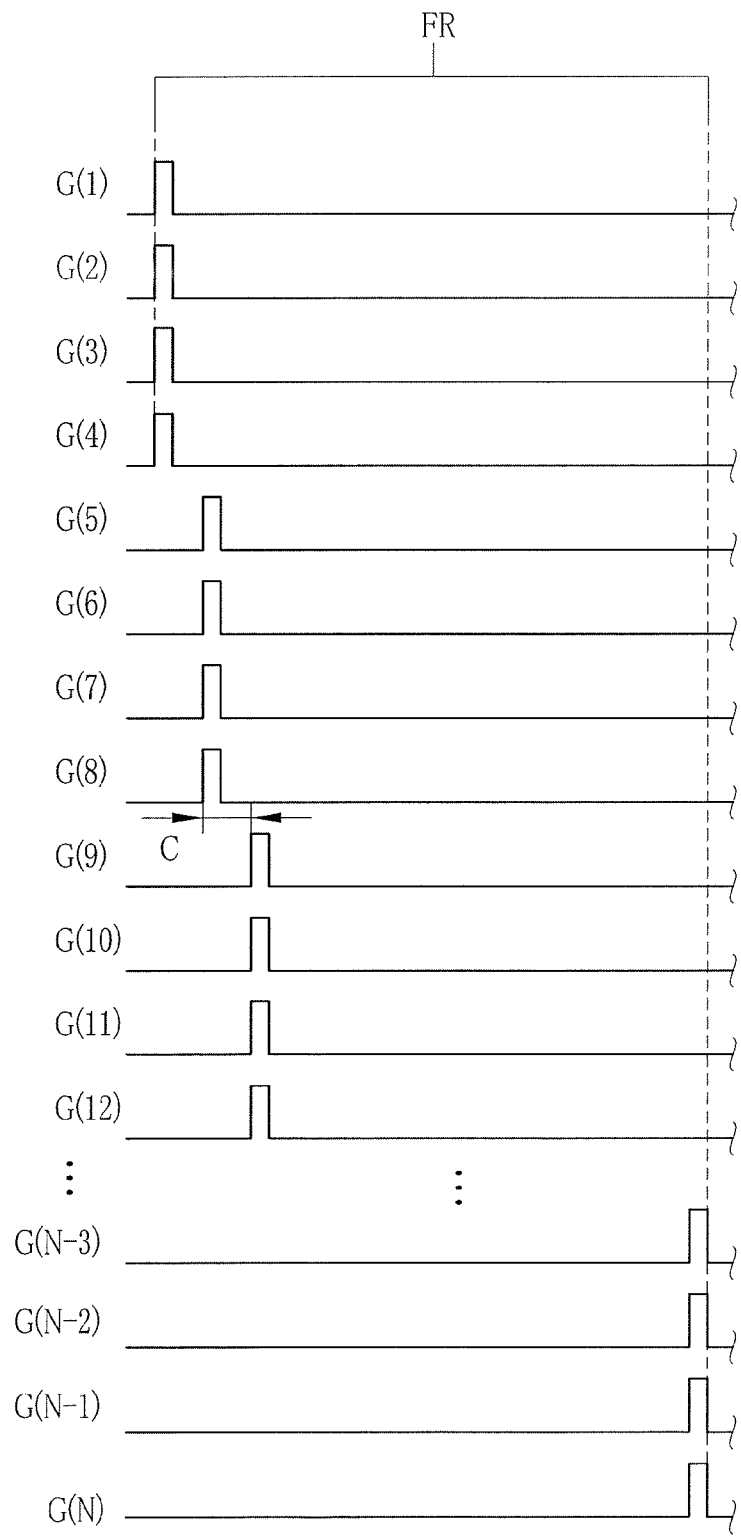
FIG. 24 is a timing chart illustrating a state of generating a gate pulse in the second mode operation in a fourth preferred embodiment.
Figure 25A:
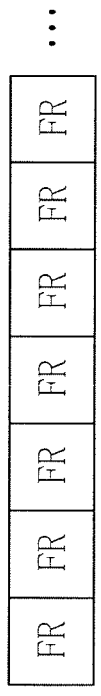
FIGS. 25A and 25B are timing charts illustrating states of generating a gate pulse in respectively the first and second mode operations.
Figure 25B:
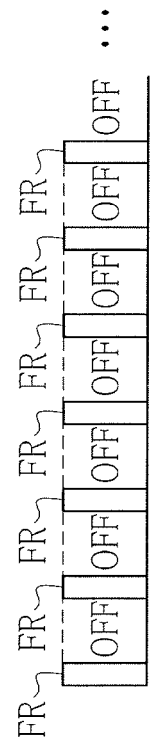

In the second mode operation, plural adjacent pixel rows are regarded as one pixel row in the controller 54, which causes the sensor panel 30 to operate in the pixel binning of a method of pixel reset in which charge of the pixels 40 of the plural adjacent pixel rows are output together. In FIG. 24, a gate pulse G (K) is generated simultaneously for the four adjacent pixel rows. The scan lines 41 are activated sequentially for each four pixel rows, to turn on the thin film transistors 45 for each four pixel rows. In FIGS. 25A and 25B, the pixel binning of a method of pixel reset is performed at a repetition period equal to that of the pixel reset FR of one frame in the first mode operation.

The time required for the pixel reset FR of one frame in the second mode operation in the pixel binning of a method of pixel reset can be reduced to ¼ of that of the first mode operation. During idle time created by the reduction, the gate driver 50 and the signal processor 51 are not powered by the battery 32. Accordingly, the time of driving the gate driver 50 and the signal processor 51 and the number of events of driving those are smaller in the second mode operation than in the first mode operation. Driving power for the second mode operation can be set lower than for the first mode operation. A dose signal from the pixel binning of a method of pixel reset is a result of adding up the charge of the pixels 40 of plural pixel rows. Thus, signal components of the dose signal can be increased more than a dose signal obtained by pixel reset by one pixel row, so that the S/N radio can be higher. It is possible to obtain auxiliary effect of increasing reliability in the level detection. Note that the interval of the pixel reset of one pixel row is C of that according to the first embodiment.

Fifth Preferred Embodiment

Figure 26:
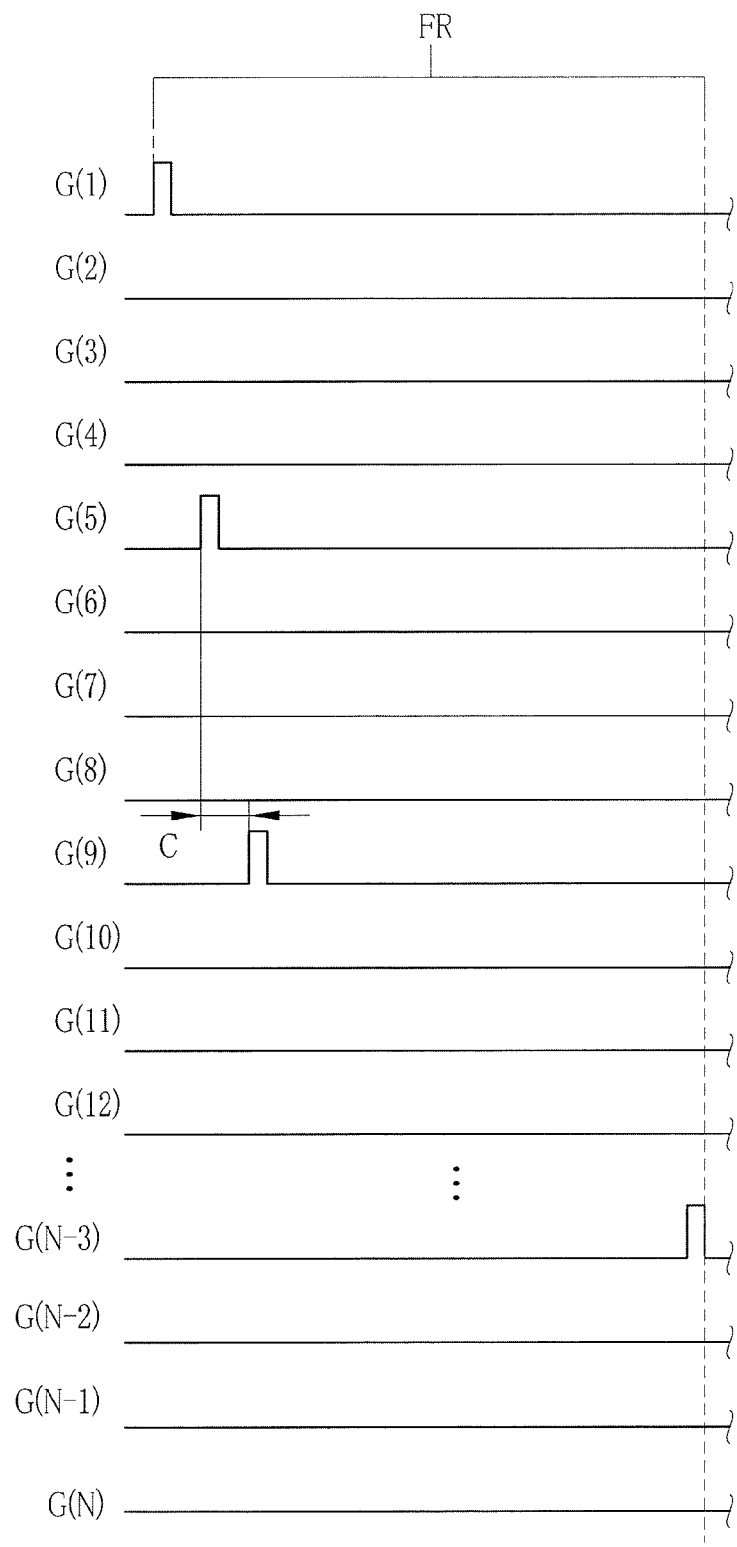
FIG. 26 is a timing chart illustrating a state of generating a gate pulse in the second mode operation in a fifth preferred embodiment.

In the second mode operation, the controller 54 in the fifth embodiment causes the sensor panel 30 to perform selective reset of a method of pixel reset in which charge of the pixels 40 of a particular pixel row is swept selectively. See FIG. 26. Generation of gate pulses G(K) is repeated for pixel rows Nos. 1, 5, 9 and so on by skipping three pixel rows regularly. The scan lines 41 are sequentially activated by skipping three pixel rows regularly to turn on the thin film transistors 45. In a manner similar to the fourth embodiment, the selective reset of a method of pixel reset is performed repeatedly and periodically at the same period of the pixel reset FR of one frame in the first mode operation. In the selective reset of a method of pixel reset, time required for the pixel reset is ¼ as long in the second mode operation as in the first mode operation. During idle time created by shortening, the gate driver 50 and the signal processor 51 are not powered by the battery 32. Thus, the same effect as the fourth embodiment can be obtained.

In the second mode operation, full pixel reset can be used instead of the sequential reset of a method of pixel reset, the pixel binning of a method of pixel reset, and the selective reset of a method of pixel reset. In the sensor panel 30 in the second mode operation, all of the pixel rows are supplied simultaneously with a gate pulse G(K) to sweep the charge from all the pixels 40 in the full pixel reset. There is a problem of saturation in a dose signal by excessive height, due to addition of the charge of the pixels 40 of all the pixel rows in the full pixel reset. In view of this, it is preferable to perform any one of the sequential reset of a method of pixel reset, the pixel binning of a method of pixel reset, and the selective reset of a method of pixel reset.

Furthermore, two or more of the above embodiments can be combined with one another. For example, it is possible to combine the feature of the second mode operation in the first embodiment with the pixel binning of a method of pixel reset of the fourth embodiment or with the selective reset of a method of pixel reset of the fifth embodiment. In the second mode operation in the first embodiment, a sequential reset of a method of pixel reset of one frame is performed at a longer interval than in the first mode operation. Thus, it is possible further to elongate idle time without power supply from the battery 32 to the gate driver 50 and the signal processor 51.

It is impossible in the second mode operation to detect the irradiation only, in contrast with the first mode operation for the purpose of precisely detecting the start of the irradiation of X-rays. Thus, there is no need of continuously outputting a dose signal in a manner of the first mode operation. Furthermore, it is possible only to output a dose signal for at least one time during the irradiation time determined with the irradiation condition.

The second mode operation is the pixel reset according to the above embodiments, but is not limited. For example, a dose signal can be created from the signal processor 51 according to the leak current from the pixels 40 while the gate driver 50 is not driven and the thin film transistors 45 are turned off. Even while the thin film transistors 45 are turned off, leak charge of a fine amount is leaked from the pixels 40 to the signal lines 42. As the leak charge increases according to an increase in the stored charge, it is possible to store the leak charge in the integrating amplifiers 55 and read this as a dose signal. Thus, the leak charge can be utilized for detection of radiation in the second mode operation. In the first mode operation, the pixel reset for one frame is performed continuously without break in the manner of the first embodiment. As the gate driver 50 is not driven, consumption power in the second mode operation is lower than in the first mode operation.

Also, an ammeter for measuring a current can be utilized. In general, a current flows on the bias line according to charge generated by the pixels 40, the bias line supplying the pixels 40 with bias voltage. In the second mode operation, the current flowing on a bias line in connection with a particular one of the pixels 40 is measured by the ammeter in a state without powering the gate driver 50 and the signal processor 51 from the battery 32. A dose signal can be output according to the measured current. As a result, driving power in the second mode operation is lower than the first mode operation.

Also, it is possible to dispose a plurality of X-ray detection sensors in the sensor panel 30 for detecting X-rays separately from the pixels. In the first mode operation, all of the X-ray detection sensors can be driven. In the second mode operation, a limited number of the X-ray detection sensors among those are driven to reduce driving power. The X-ray detection sensors can be disposed on or around the active pixel area 43 of the sensor panel 30, inside or outside a housing of the electronic cassette 12 except for the active pixel area 43, and the like.

It is concluded that any of various methods can be used for the second mode operation on the condition of lower driving power than the first mode operation. The second mode operation is not limited to the control of the sensor panel, but can be control of any one of circuit elements included in the electronic cassette, such as a communication interface, memory and the like, to set the driving power lower than in the first mode operation.

In the first embodiment, the function for detecting start of irradiation is provided in the electronic cassette 12, for synchronizing the start of irradiation from the X-ray source 15 with a start of storing in the sensor panel 30. Instead of or in addition to the detecting function, a sync function for transferring a sync signal can be provided in the electronic cassette 12 for the purpose of transmitting and receiving the sync signal with the imaging control unit 13 for synchronizing the start of irradiation from the X-ray source 15 with a start of storing.

To use the sync function, the detection of starting the irradiation is not required in the selected cassette. The normal pixel reset is performed as first mode operation. In the normal pixel reset, the controller 54 outputs an amplifier reset pulse in synchronism with the fall of the gate pulse G(K) to turn on the amplifier reset switch 55c. Dark current charge is discharged from the capacitor 55b, to reset the integrating amplifiers 55. Therefore, no dose signal is output in the manner of the above embodiments. The remainder of the operation is the same as the first embodiment. It is noted that a first cassette with the function for detecting the start of the irradiation can be disposed with a second cassette with the sync function in an imaging room together.

In the sensor panel of the first embodiment, the scintillator 36 is disposed upstream of the light receiving unit 37 according to the entry of X-rays. However, a sensor panel can be so constructed that the scintillator 36 is disposed downstream of the light receiving unit 37. The scintillator 36 absorbs X-rays transmitted through the light receiving unit 37 and generates visible light, which the light receiving unit 37 converts photoelectrically into signal charge.

In the first embodiment, X-rays are converted into visible light, which is converted into signal charge. The sensor panel 30 is the indirect conversion type. However, a sensor panel of the invention may be a direct conversion type for directly converting X-rays into signal charge by use of amorphous selenium or the like as photoconductive film.

The sensor panel of the first embodiment is the TFT type. However, a sensor panel of the invention can be a CMOS type (complementary metal oxide semiconductor). In the first embodiment, the imaging control unit 13 is separate from the console unit 14. However, a single unit can include components of the imaging control unit 13 and the console unit 14.

The feature of the invention can be used in the radiographic image detector of a stationary type placed on the floor stand in contrast with the cassette as a portable type of the radiographic image detector. The radiographic image detector of the stationary type cannot be exchanged. An operator, assuming that the selection of the electronic cassette 12 is erroneous, can only reselect the electronic cassette 12 by use of the selection screen 26. Thus, the second embodiment is typically effective for the stationary type of the radiographic image detector with the floor stand.

Also, radiation for use in the radiographic imaging of the invention can be gamma rays or the like other than X-rays.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic imaging system including a plurality of radiographic image detectors each of which has a sensor panel for detecting a radiographic image according to radiation, and a user input interface for selecting one of said plural radiographic image detectors for use in imaging, said radiographic imaging system comprising:
a controller, associated with each of said radiographic image detectors, for performing a first mode operation for said radiographic image detector in case a selected state is set according to said user input interface, and performing a second mode operation for said radiographic image detector in case an unselected state is set according to said user input interface, where driving power in said second mode operation is lower than in said first mode operation for detecting irradiation of said radiation; and
a display device for, assuming that irradiation of said radiation is detected in said second mode operation, displaying error information in relation to selecting said radiographic image detector with said user input interface,
wherein in said first mode operation, said radiographic image detector outputs a dose signal that represents a dose of an incident radiation reaching said sensor panel, and
wherein in said second mode operation, the output frequency of said dose signal per unit time is lower than that in said first mode operation.

2. A radiographic imaging system as defined in claim 1, wherein said user input interface selectively generates a selection signal of said selected state of said radiographic image detector and a non-selection signal of said unselected state of said radiographic image detector;
each of said radiographic image detectors has a communication interface for receiving said selection signal and said non-selection signal;
said controller selects said first mode operation upon receiving said selection signal, and selects said second mode operation upon receiving said non-selection signal.

3. A radiographic imaging system as defined in claim 2, wherein before said communication interface receives said selection or non-selection signal, powering of said sensor panel is turned off, and in case said communication interface receives said selection or non-selection signal, said sensor panel starts being powered to start said first or second mode operation.

4. A radiographic imaging system as defined in claim 2, wherein said radiographic image detector is wirelessly on-line with a related apparatus by use of said communication interface, and is supplied with power by a battery.

5. A radiographic imaging system as defined in claim 2, wherein said first mode operation is detection of a start of irradiation of said radiation.

6. A radiographic imaging system as defined in claim 2, wherein said sensor panel includes a panel device having pixels arranged two-dimensionally for storing signal charge upon receiving said radiation, and a signal processor for converting said signal charge into an image signal to generate said radiographic image;
at least one of said first and second mode operations includes pixel reset in which charge stored in said pixels is swept in said panel device;
said radiographic image detector includes a level detection device for detecting irradiation of said radiation according to said charge swept in said pixel reset.

7. A radiographic imaging system as defined in claim 6, wherein said signal processor converts said charge swept in said pixel reset into a dose signal of a dose of said radiation reaching said panel device, and transmits said dose signal to said level detection device.

8. A radiographic imaging system as defined in claim 6, wherein said first mode operation is sequential reset of a method of pixel reset in which charge of said pixels is swept by one pixel row from a first pixel row to a final pixel row in said sensor panel, and said charge of one frame is swept by sweeping said charge of said final pixel row so as to repeat sweep of said charge by returning to said first pixel row.

9. A radiographic imaging system as defined in claim 8, wherein said second mode operation is said sequential reset of said method of said pixel reset in said sensor panel.

10. A radiographic imaging system as defined in claim 9, wherein said sequential reset of said method of said pixel reset for one frame is performed at a longer interval in said second mode operation than in said first mode operation.

11. A radiographic imaging system as defined in claim 9, wherein said sequential reset of said method of said pixel reset for one pixel row is performed at a longer interval in said second mode operation than in said first mode operation.

12. A radiographic imaging system as defined in claim 6, wherein said second mode operation is pixel binning of a method of pixel reset in which said charge of pixels of plural adjacent pixel rows are swept together in said sensor panel.

13. A radiographic imaging system as defined in claim 6, wherein said second mode operation is selective reset of a method of pixel reset in which said charge stored in said pixels of particular pixel rows are selectively swept in said sensor panel.

14. A radiographic imaging system as defined in claim 6, further comprising an artifact corrector for estimating a lag value of next imaging according to lag value information of a relationship between a lag value from residual charge in said pixels in preceding imaging and elapsed time from said preceding imaging, and for correcting said radiographic image in artifact correction of image lag according to said estimated lag value.

15. A radiographic imaging system as defined in claim 14, wherein assuming that irradiation of said radiation is detected in said second mode operation, said artifact corrector updates said lag value information in consideration of said lag value upon detection, to use said updated lag value information for said artifact correction of image lag.

16. A radiographic imaging system as defined in claim 14, wherein said artifact corrector updates said lag value information according to first and second time points;
said first time point is a time point where irradiation of said radiation in said second mode operation is detected by a first radiographic image detector unselected according to said user input interface among said plural radiographic image detectors;
said second time point is later than said first time point, and is a time point where irradiation of said radiation in said first mode operation is detected by said first radiographic image detector for next imaging upon selecting said first radiographic image detector according to said user input interface.

17. A system operation method for a plurality of radiographic image detectors for detecting a radiographic image, comprising steps of:
selecting one of said plural radiographic image detectors for use in imaging by input operation;
performing a first mode operation for said radiographic image detector selected in said selected step;
performing a second mode operation for one of said radiographic image detectors unselected in said selecting step, where driving power in said second mode operation is lower than in said first mode operation for detecting irradiation of said radiation; and
assuming that irradiation of said radiation is detected in said second mode operation, displaying error information in relation to selecting said radiographic image detector in said selecting step,
wherein in said first mode operation, said radiographic image detector outputs a dose signal that represents a dose of an incident radiation reaching said sensor panel, and
wherein in said second mode operation, the output frequency of said dose signal per unit time is lower than that in said first mode operation.

* * * * *